United States Patent [19]
Lampert

[11] Patent Number: 5,823,194
[45] Date of Patent: Oct. 20, 1998

[54] FLEXIBLE RETENTIVE BITE BLOCK AND FABRICATION PROCESS

[76] Inventor: Barry Lampert, 34 Watchway, Lloyd Harbor, N.Y. 11743

[21] Appl. No.: 847,060

[22] Filed: May 1, 1997

[51] Int. Cl.⁶ ........................................................ A61F 5/56
[52] U.S. Cl. ............................ 128/848; 128/859; 128/861
[58] Field of Search ............................ 128/848, 859–862; 2/2; 433/6

[56] References Cited

U.S. PATENT DOCUMENTS

| | | | |
|---|---|---|---|
| 5,203,324 | 4/1993 | Kinkade | 128/201.11 |
| 5,365,945 | 11/1994 | Halstrom | 128/848 |
| 5,409,017 | 4/1995 | Lowe | 128/848 |
| 5,409,067 | 4/1995 | Lowe | 128/848 |
| 5,427,117 | 6/1995 | Thornton | 128/848 |
| 5,499,633 | 3/1996 | Fenton | 128/848 |
| 5,562,106 | 10/1996 | Heeke et al. | 128/848 |
| 5,566,683 | 10/1996 | Thornton | 128/848 |

Primary Examiner—Michael A. Brown
Attorney, Agent, or Firm—Richard L. Miller

[57] ABSTRACT

A dentally retained intra-oral appliance worn at night for treatment of snoring and obstructive sleep apnea and its fabrication process. The appliance maintains the patient's mandible in an anterior, protruded position to prevent obstruction of the pharyngeal airway. The appliance allows a limited degree of lateral movement of the mandible relative to the upper jaw in the protruded position to prevent aggravation of the patient's temporomandibular joint and associated muscles and ligaments. The appliance includes a lower bite block conforming to the patient's mandibular dentition, an upper bite block conforming to the patient's maxillary dentition, and a hinge connecting the upper bite block to the lower bite block. The upper bite block and the lower bite block are thin walled polyamide eliminating the need for dental wires to maintain them to the mandibular detention and the maxillary dentition and the problems associated therewith.

25 Claims, 43 Drawing Sheets

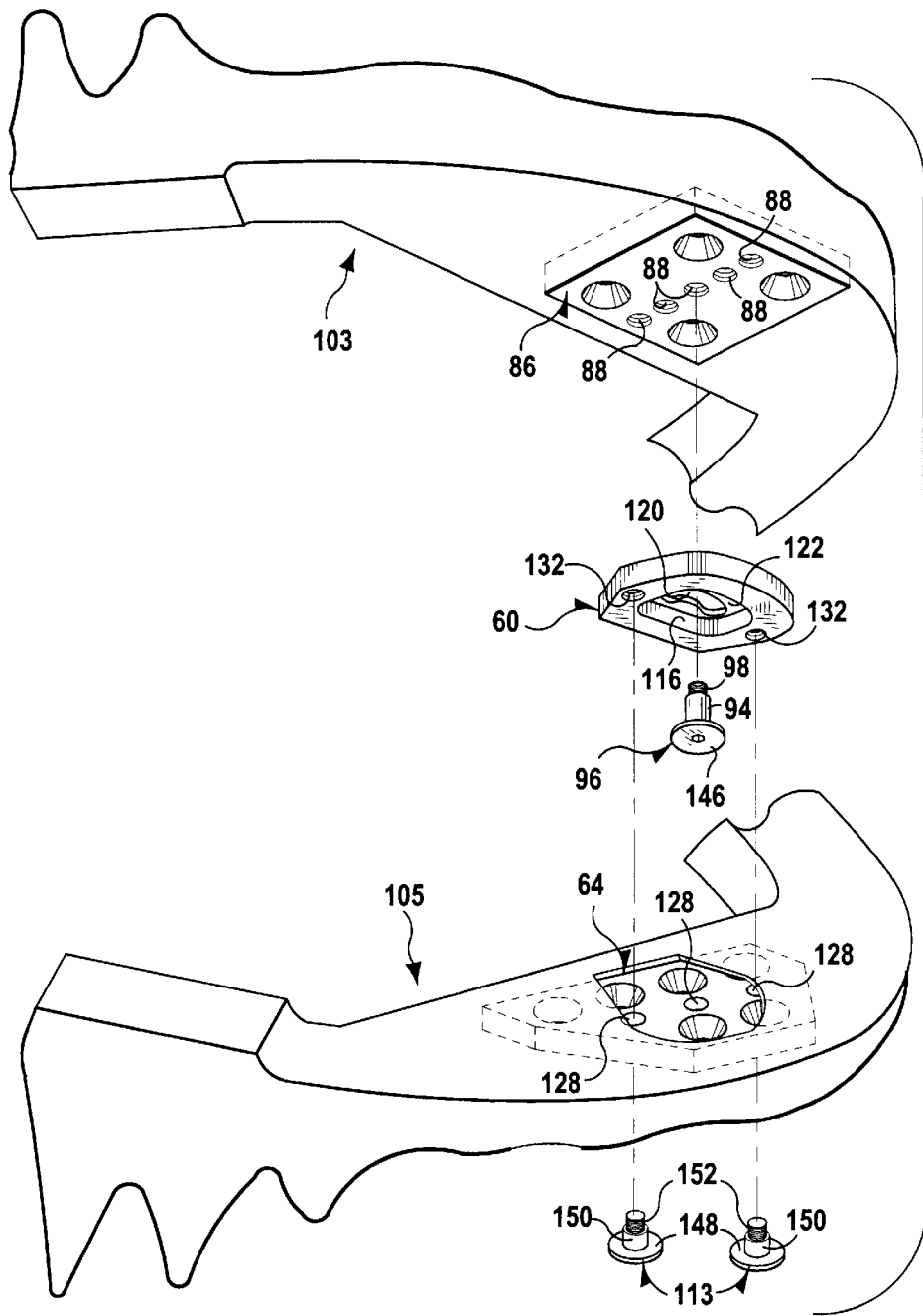

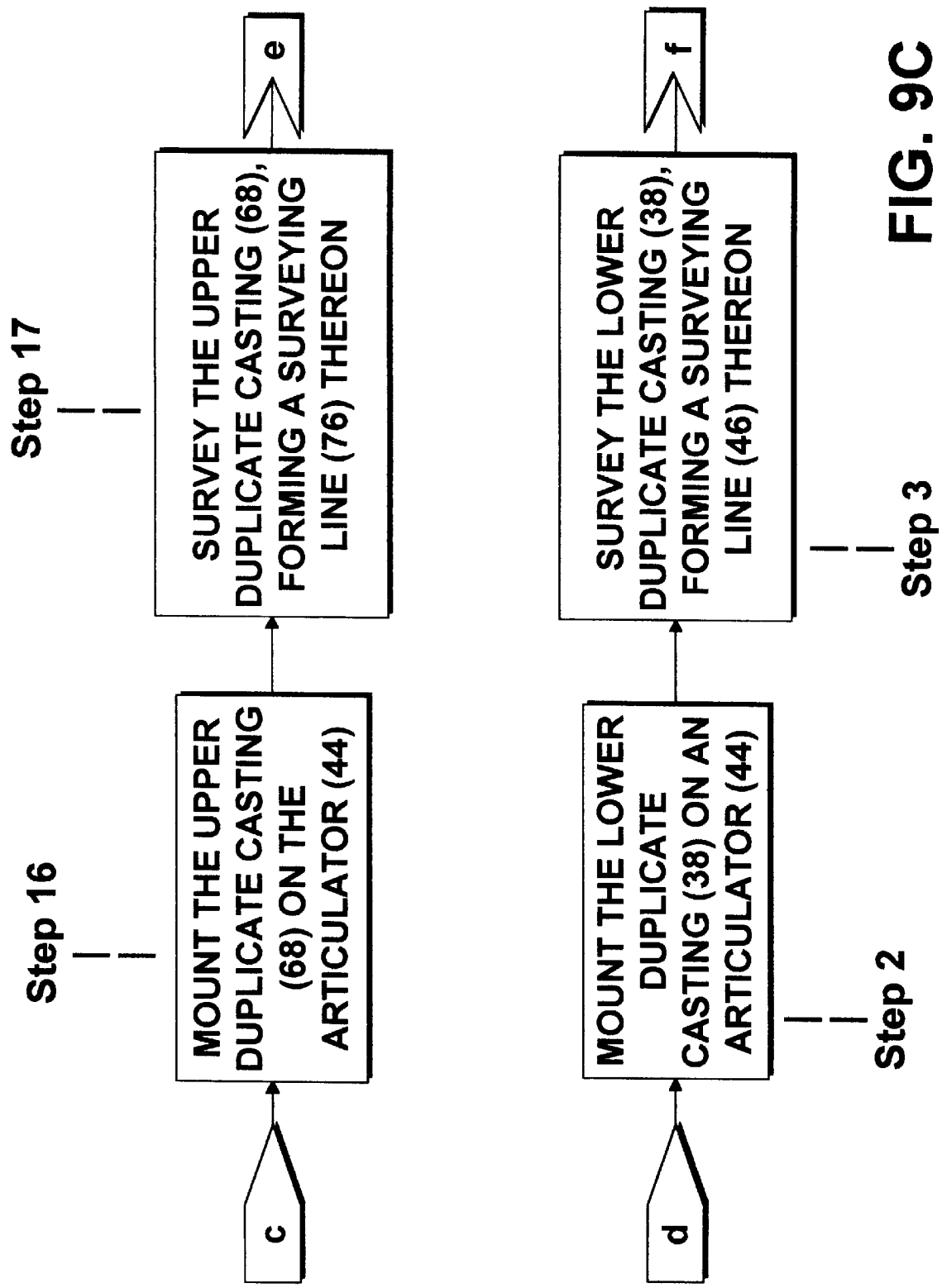

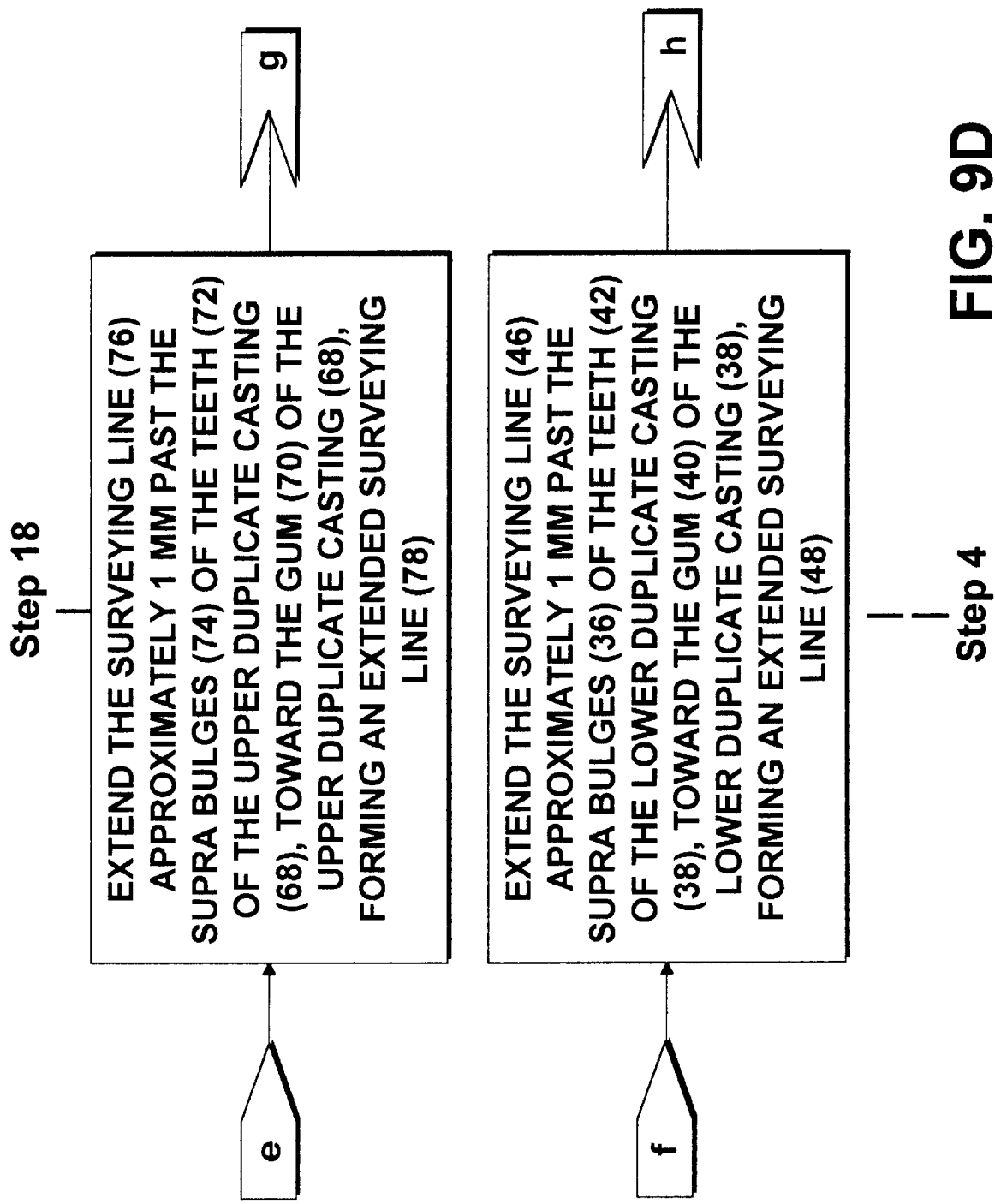

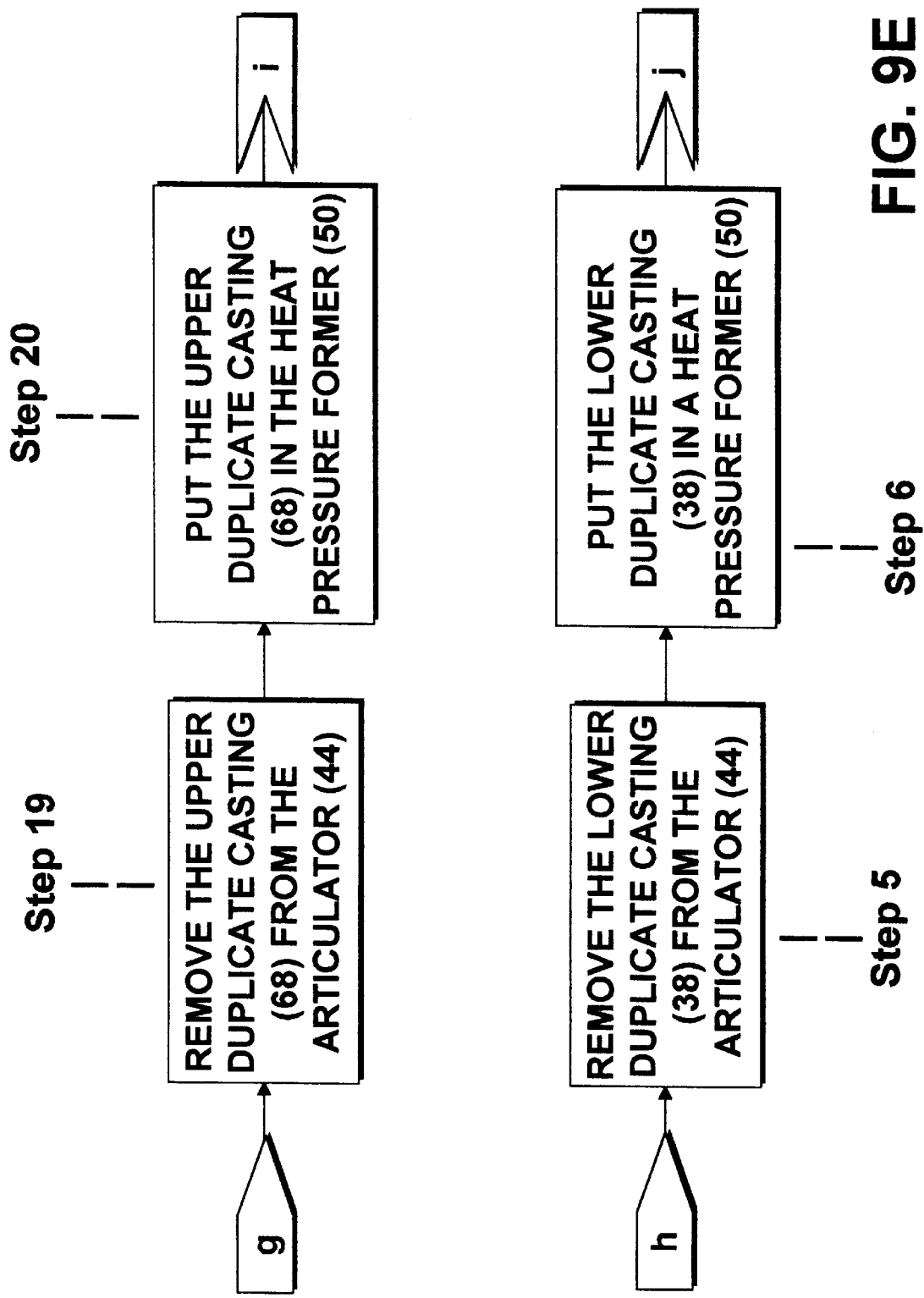

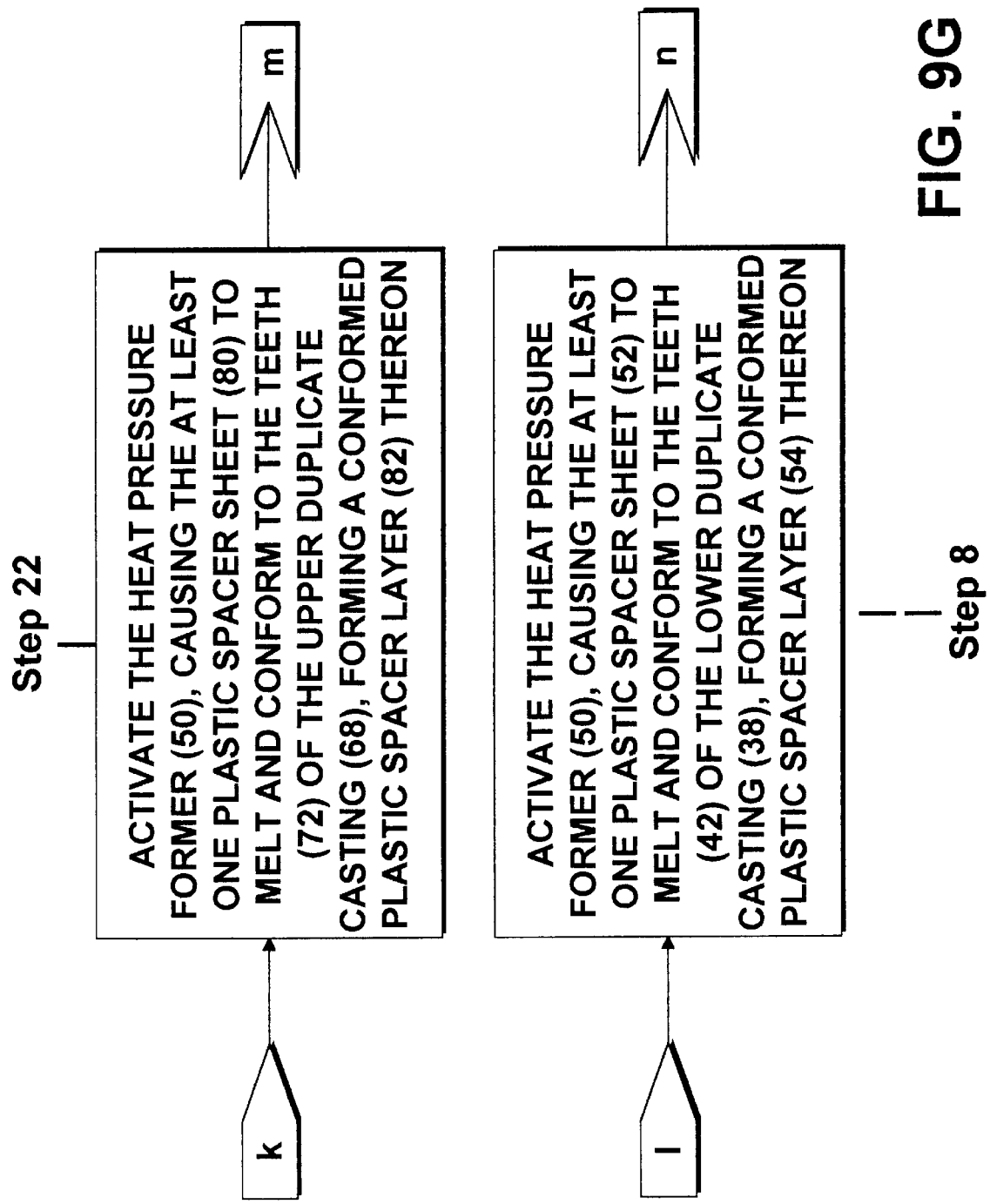

Step 25: REPLACE THE UPPER DUPLICATE CASTING (68) WITH THE UPPER PATTERN (85) THEREON ON THE ARTICULATOR (44)
Step 11: REPLACE THE LOWER DUPLICATE CASTING (38) WITH THE LOWER PATTERN (57) THEREON ON THE ARTICULATOR (44)
FIG. 9J

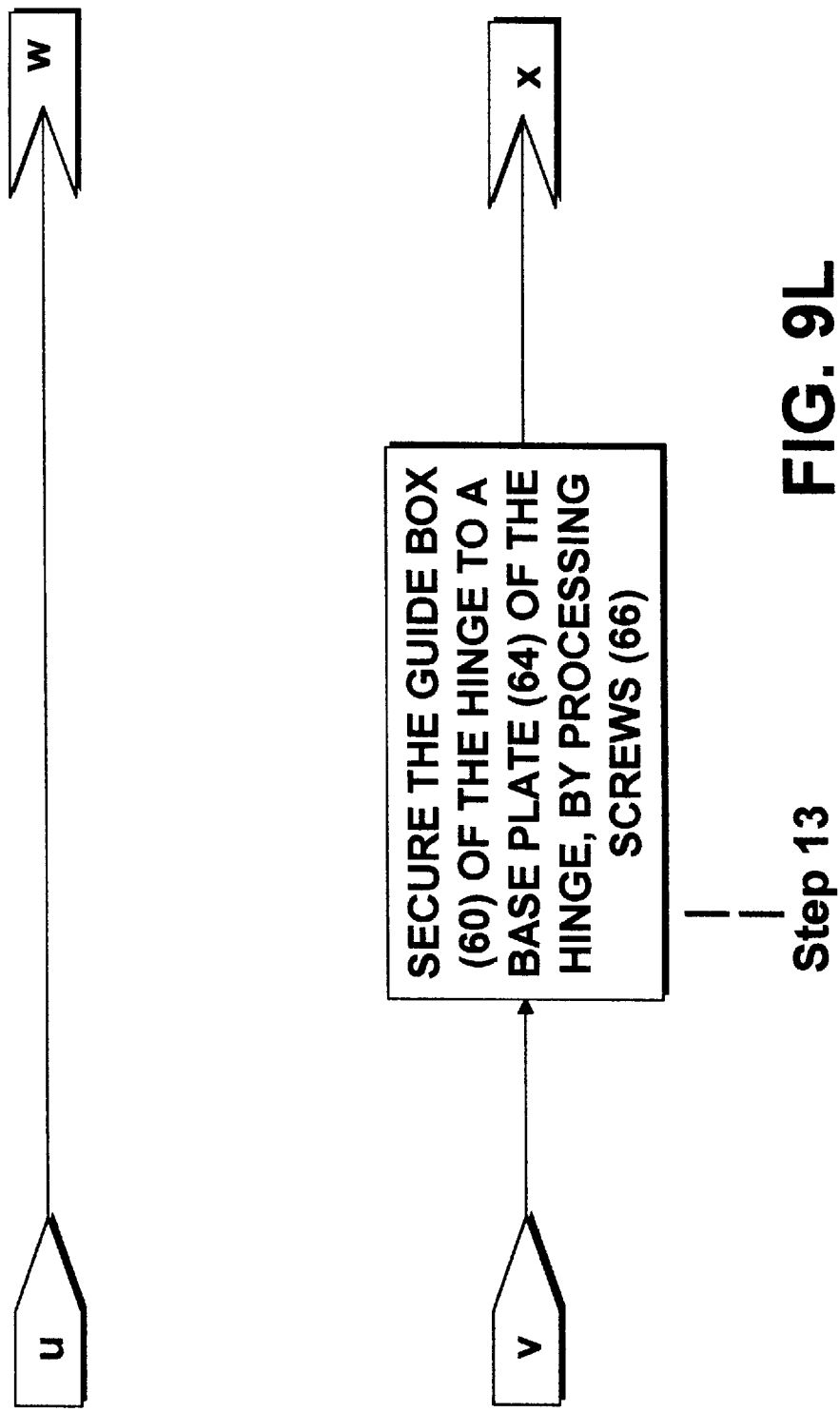

SECURE THE BASE PLATE (64) OF THE HINGE TO THE LOWER DUPLICATE CASTING (38), UTILIZING THE WAX LUTING AGENT, FORMING A LOWER ASSEMBLAGE (67)

Step 14

FIG. 9O

Step 27 aa → SECURE THE RETENTION PLATE (86) OF THE HINGE TO THE UPPER PATTERN (85), UTILIZING THE WAX LUTING AGENT → bb

Step 28 — POSITION A PART (90) OF AN UPPER PROCESSING JIG (92) INTO THE RETENTION PLATE (86) OF THE HINGE

FIG. 9Q

Step 29

SECURE THE UPPER PROCESSING JIG (92) TO THE RETENTION PLATE (86), BY PASSING A NON-THREADED PORTION (94) OF A FINAL STYLUS (96) THROUGH THE UPPER PROCESSING JIG (92), WITH A THREADED PORTION (98) OF THE FINAL STYLUS (96) THREADABLY ENGAGING THE APERTURE (88) IN THE RETENTION PLATE (86), FORMING AN UPPER ASSEMBLAGE (100)

cc → (into step) → dd, ee

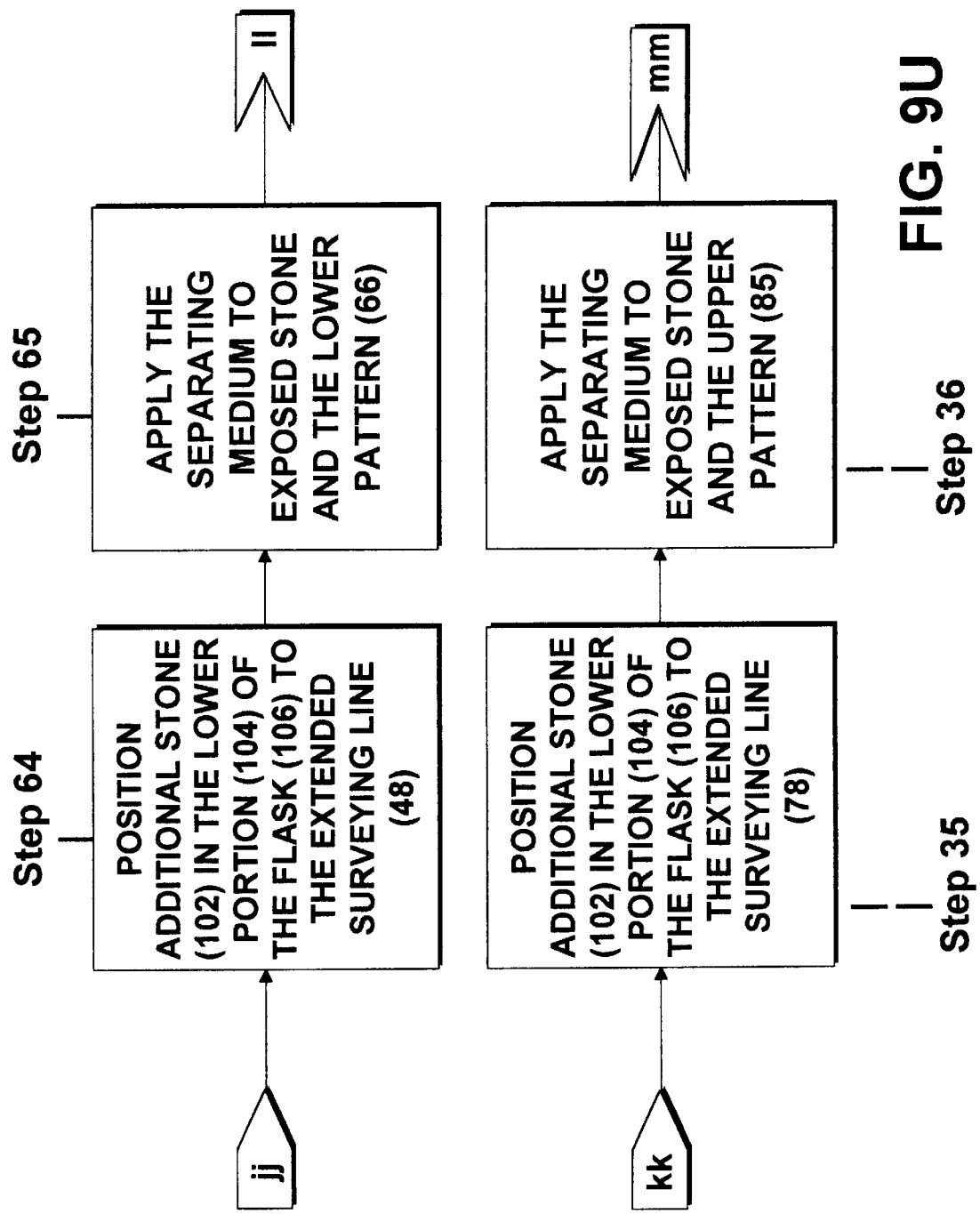

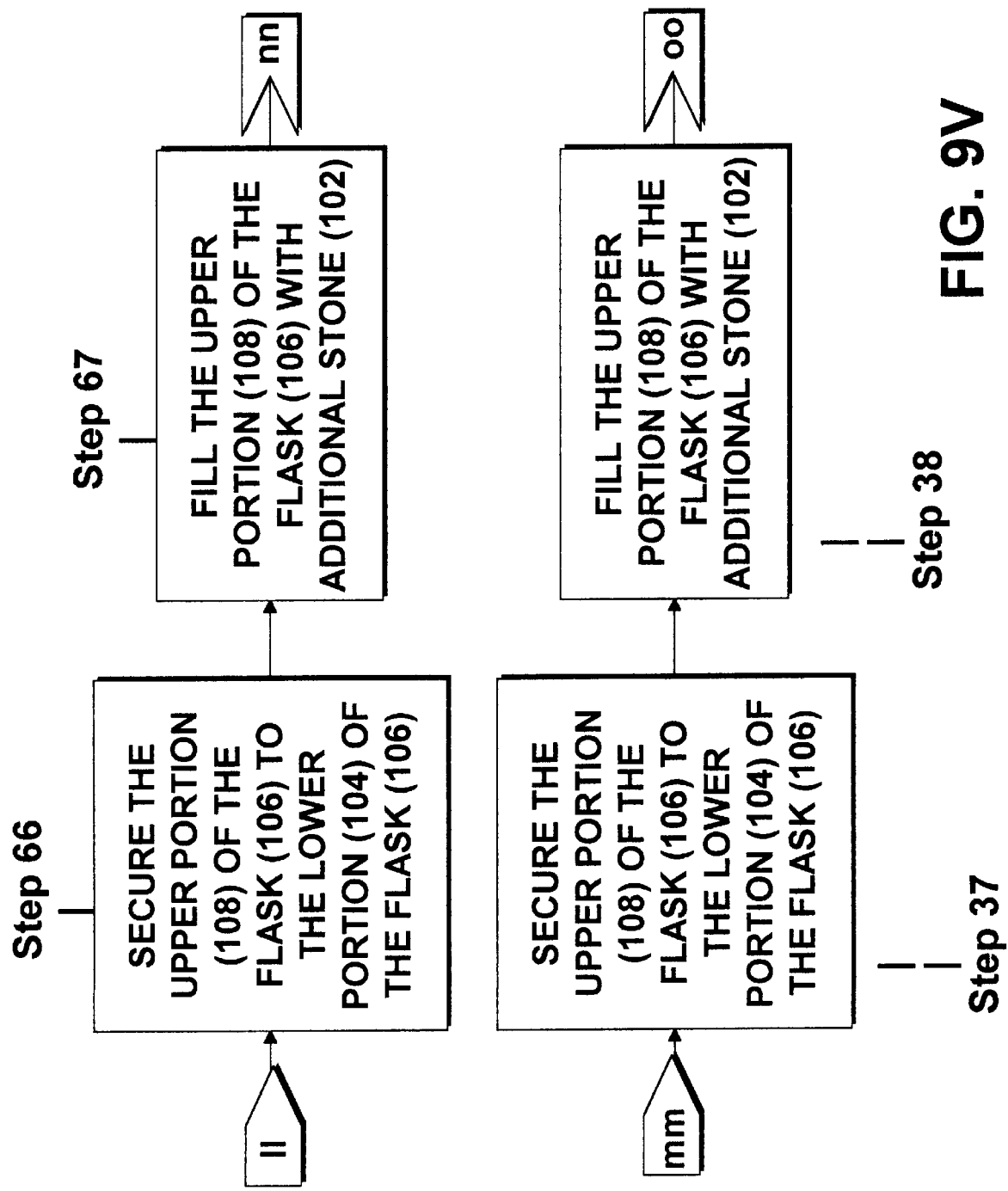

Step 71

PICK OUT THE CONFORMED PLASTIC SPACER LAYER (54) AND THE PAIR OF OPPOSING METAL BITE PADS (56) FROM THE LOWER BITE BLOCK MOLD

→ vv tt →

Step 42

PICK OUT THE CONFORMED PLASTIC SPACER LAYER (80) AND THE PAIR OF OPPOSING METAL BITE PADS (84) FROM THE UPPER BITE BLOCK MOLD

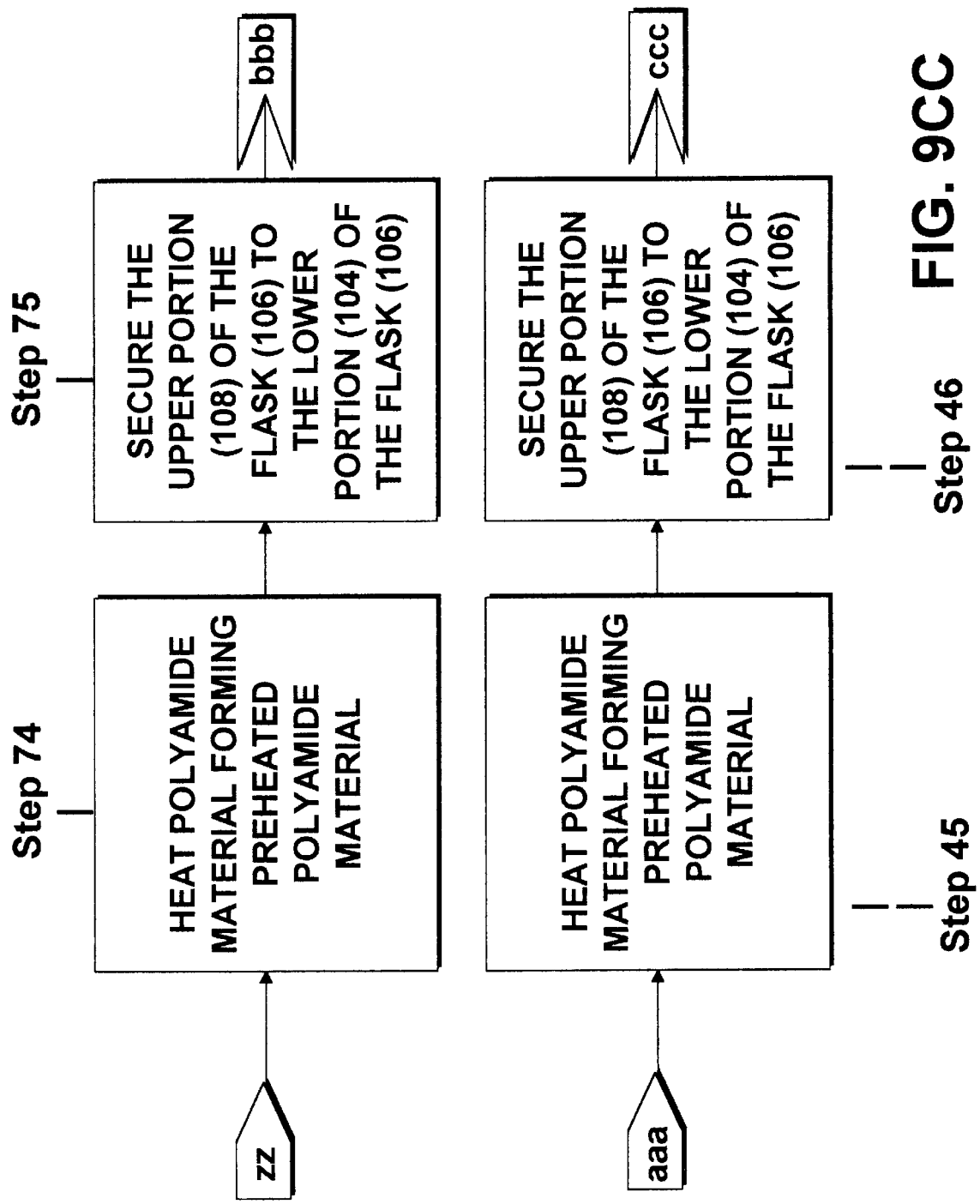

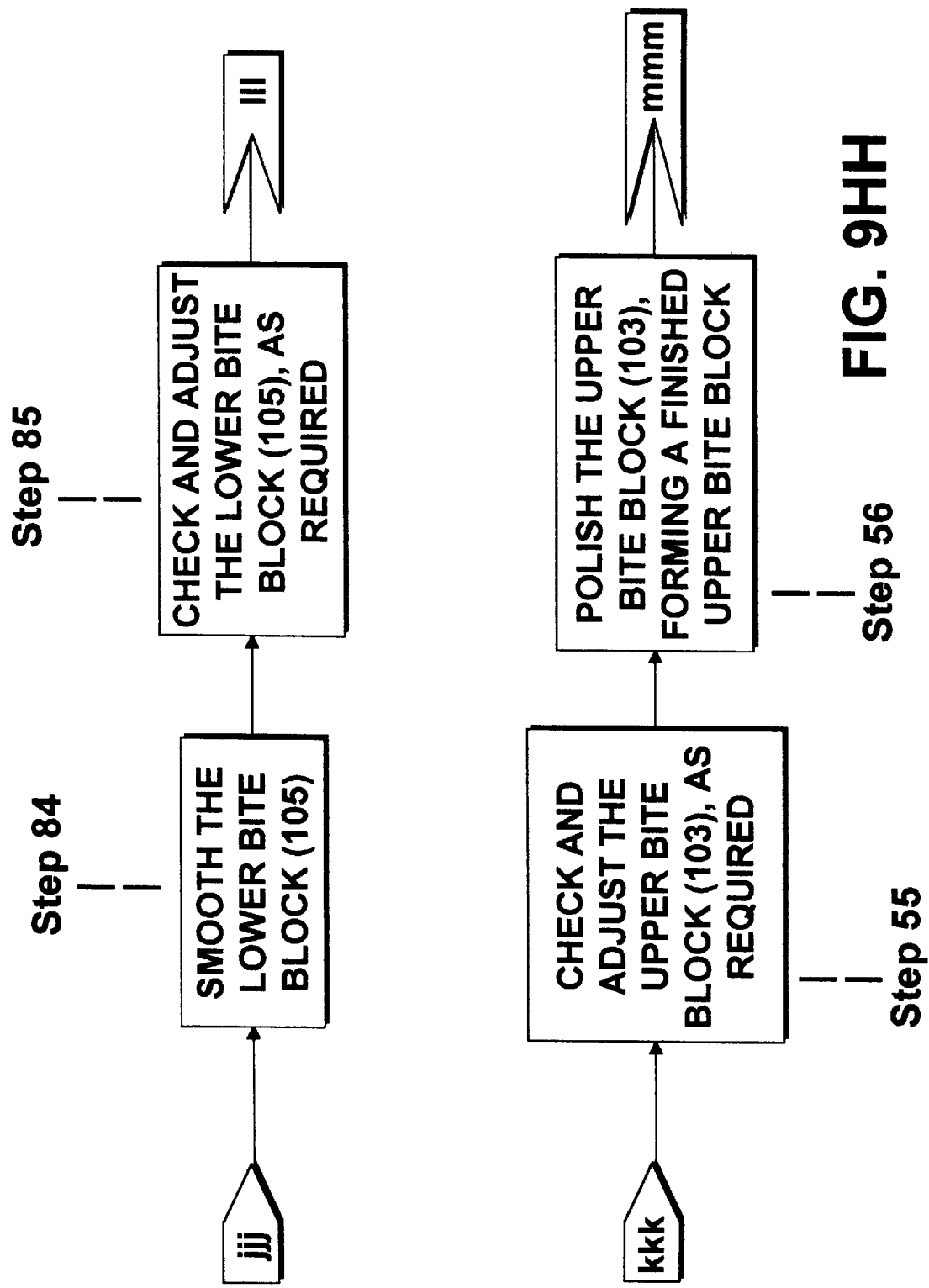

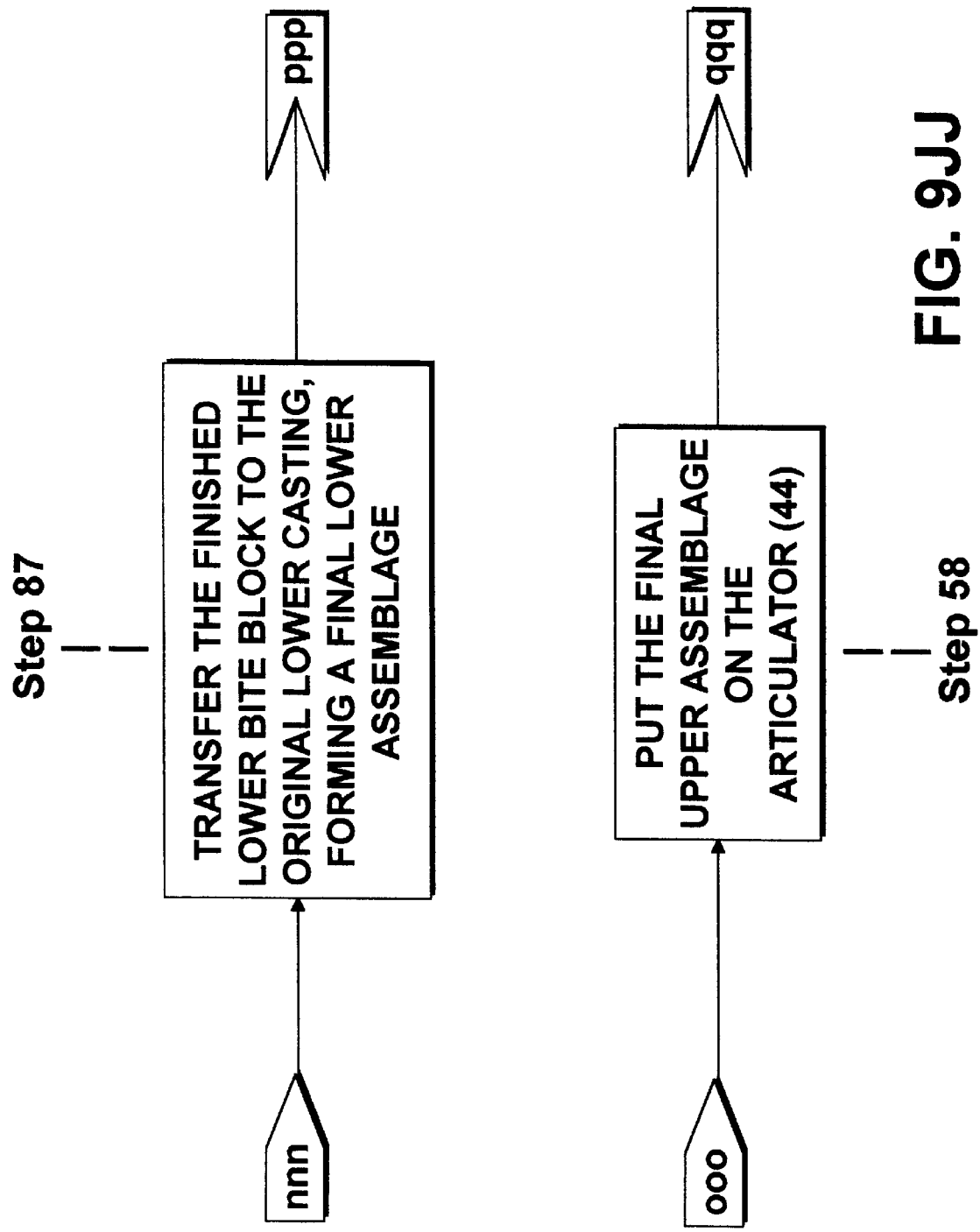

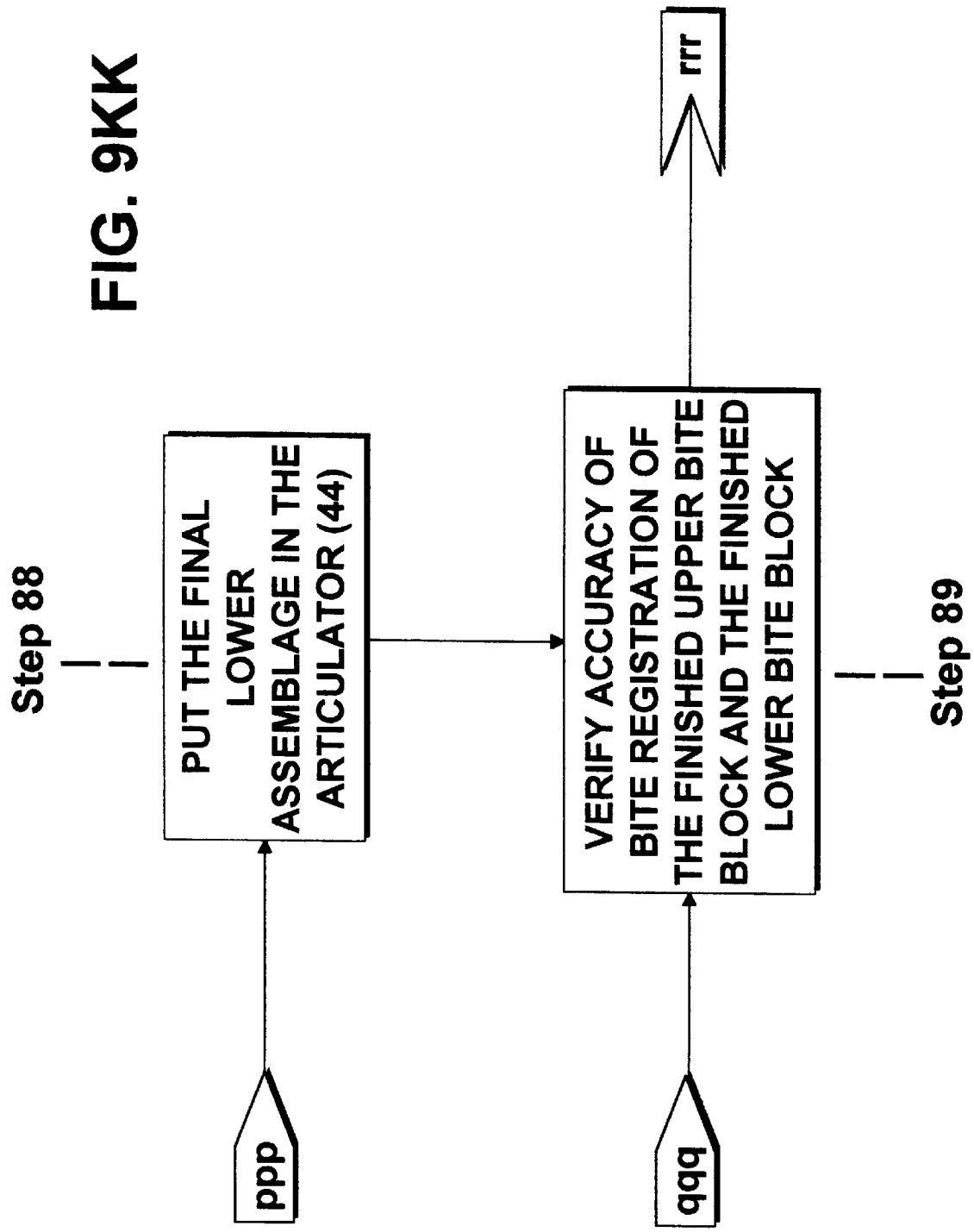

FLEXIBLE RETENTIVE BITE BLOCK AND FABRICATION PROCESS

BACKGROUND OF THE INVENTION

1. Field of the Invention

The present invention relates to a bite block. More particularly, the present invention relates to a flexible retentive bite block and fabrication process.

2. Description of the Prior Art

Snoring and Obstructive sleep apnea are typically caused by complete or partial obstruction of an individuals pharyngeal airway during sleep. Usually, airway obstruction results from the apposition of the rear portion of the tongue or soft palate with the posterior pharyngeal wall.

Obstructive sleep apnea is a potentially lethal disorder in which breathing stops during sleep for 10 seconds or more, sometimes up to 300 times per night. Snoring occurs when the pharyngeal airway is partially obstructed, resulting in vibration of the oral tissues during respiration. These sleep disorders tend to become more severe as patients grow older, likely as a result of a progressive loss of muscle tone in the patient's throat and oral tissues.

Habitual snoring and sleep apnea have been associated with other potentially serious medical conditions, such as hypertension, ischemic heart disease and strokes. Accordingly, early diagnosis and treatment is recommended.

One surgical approach, known as uvulopalatopharyngoplasty, involves removal of a portion of the soft palate to prevent closure of the pharyngeal airway during sleep. This operation, however, is not always effective and may result in undesirable complications, such as nasal regurgitation.

A wide variety of non-surgical approaches for treating sleep disorders have been proposed including the use of oral cavity appliances. It has been previously recognized that movement of the mandible (lower jaw) forward relative to the maxilla (upper jaw) can eliminate or reduce sleep apnea and snoring symptoms by causing the pharyngeal air passage to remain open.

Several intra-oral dental appliances have been developed which the user wears at night to fix the mandible in an anterior, protruded (i.e. forward) position. Such dental appliances essentially consist of acrylic or elastomeric bite blocks, similar to orthodontic retainers or athletic mouth guards, which are custom-fitted to the user's upper and lower teeth and which may be adjusted to vary the degree of anterior protrusion.

While prior art dental appliances have proven effective in maintaining the mandible in a protruded position to improve airway patency, they often result in undesirable side effects. One of the most common side effects is aggravation of the temporomandibular joint and related jaw muscles and ligaments, especially in individuals who have a tendency to grind their teeth during sleep.

Aggravation of the temporomandibular joint has been associated with a wide variety of physical aliments, including migraine headaches. Accordingly, many individuals suffering from sleep apnea and snoring disorders are not able to tolerate existing anti-snoring dental appliances for long periods of time.

The need has therefore arisen for a dental appliance for treatment of snoring and sleep apnea which will maintain the mandible in a preferred anterior position, allow a limited degree of lateral excursion of the mandible relative to the upper jaw to avoid discomfort to the temporomandibular joint and related muscles and ligaments, and be replaceably maintained on the user's teeth by virtue of its own flexibility and thereby eliminating the need for dental wires that can aggravate the teeth and gums and which requires the appliance to have thick walls for their support which can lead to further discomfort for the user, such as gum and cheek irritation and gagging.

Numerous innovations for mouthpieces have been provided in the prior art that will be described. Even though these innovations may be suitable for the specific individual purposes to which they address, however, they differ from the present invention.

FOR EXAMPLE, U.S. Pat. No. 5,203,324 to Kinkade teaches a mouthpiece for use in diving or medical equipment, among others made of moldable resilient material having an offset between upper and lower jaw, a bite plane which is tapered with the bite plane formed by wings which have varying thickness to create the taper in which the wing members have substantially vertical surfaces on either side thereof for contacting the lateral surfaces of the user's cuspids and bicuspids and in which the main body portion has upper and lower apron and eminence skirts for avoiding contact with the user's frenum and cuspid eminences and in which the internal wing members have a range in size, at the cuspid, from about 6 to about 12 mm in width, from about 14 to about 40 mm in length and from about 2 mm to about 8 mm in thickness. The greater the offset, the shorter the length of the internal wind members.

ANOTHER EXAMPLE, U.S. Pat. No. 5,365,945 to Halstrom teaches a dentally retained intra-oral appliance worn at night for treatment of snoring and obstructive sleep apnea. The appliance maintains the patient's mandible in an anterior, protruded position to prevent obstruction of the pharyngeal airway. The appliance allows a limited degree of lateral movement of the mandible relative to the upper jaw in the protruded position to prevent aggravation of the patient's temporomandibular joint and associated muscles and ligaments.

As shown in FIG. 1, the appliance 10 preferably consists of a lower bite block 12 conforming to the patient's mandibular dentition 14, an upper bite block (not shown, but constructed similar to the lower bite block 12) conforming to the patient's maxillary dentition (not shown), and a connecting assembly (not shown) secured to an anterior region (not shown) of the upper (not shown) and lower bite blocks 12.

Unfortunately, the apparatus 10 requires dental wires 16 to maintain it to the mandibular detention 14 and the maxillary dentition (not shown). The dental wires 16 are embedded in the appliance 10 and bias against the mandibular detention 14 and the maxillary dentition (not shown), causing discomfort to the wearer, especially those with sensitive teeth. To support the dental wires 16, the walls 20 of the appliance 10 are thick, which lead to further discomfort for the user, such as inter alia gum, tongue, palate, and cheek irritation.

With the dental wires 16 being biased when worn, they are under stress and exert a stress on the walls 20 of the appliance 10 housing them. The stress can cause the walls 12 of the appliance 10 to fracture, splinter, or cause the dental wires 16 to separate from the appliance.

Furthermore, the appliance 10 includes a pair of opposing bite pads 22 that are separate and affixed on the biting surfaces 24 of the posterior portions 26 of the appliance 10; they are thereby subject to dislodgement from the appliance 10.

In contradistinction, however, as shown in FIG. 2, the flexible retention bite block 30 of the present invention requires no dental wires to maintain it to the mandibular detention 14 and the maxillary dentition (not shown), eliminating discomfort to the wearer, especially those with sensitive teeth. Absent the dental wires, the walls 32 of the appliance 10 are thin, eliminating further discomfort to the user, such as inter alia gum, tongue, and cheek irritation.

Absent the dental wires and the biasing associated therewith, no stress is exerted on the walls 32 of the flexible retention bite block 30, eliminating fracture, splinter, of the walls 32.

Furthermore, the flexible retention bite block 30 includes a pair of opposing bite pads 34 that are integrally formed on the biting surfaces 24 of the posterior portions 26 of the flexible retentive bite block 30; they are therefore not subject to dislodgement from the flexible retention bite block 30.

The flexible retentive bite block 30 is maintained on the mandibular detention 14 and the maxillary dentition (not shown), by virtue of its side walls 32 extending 1 mm past and capturing the supra bulge 36 of the mandibular detention 14 and the maxillary dentition (not shown), and the inherent flexibility of the polyamide material it is made of.

STILL ANOTHER EXAMPLE, U.S. Pat. No. 5,409,017 to Lowe teaches a mandible repositioning appliance formed by an upper bite block and a lower bite block interconnected by an adjustable mechanism including a posterior section connected to the rear portion of the upper bite block and an anterior section connected to the front portion of the lower bite block and an adjustable interconnection between the anterior and posterior sections. Preferably, the adjustable interconnection includes a double thread element rotation of which changes the relative positions of the posterior and interior sections axially of the appliance and abutments to define each incremental rotation of the element. The comfort of the wearer is further improved by using a heat sensitive material in the tooth retention sections and by permitting limited relative lateral movement between the bite blocks.

YET ANOTHER EXAMPLE, U.S. Pat. No. 5,499,633 to Fenton teaches an adjustable oral device for placement within the mouth of a user to reduce or eliminate snoring. The device comprises an upper member having a substantially curved shape and defining an upwardly oriented channel for receiving at least some of the upper teeth of a user. A lower member has a substantially curved shape and defines a downwardly oriented channel for receiving at least some of the lower teeth of a user. The upper member is adjustably coupled by the user to the lower member in a spaced relationship such that the lower member is positioned relative to the upper member so that when the user's teeth are retained within the device, the user's lower jaw is biased substantially forward of its normal biting or resting position to reduce snoring. The device can include an anterior tongue space between the upper and lower members, and can further include moldable material positioned within at least one of the channels for substantially conforming to a shape of the teeth, thus allowing the device to be customized for individual users.

FINALLY, YET STILL ANOTHER EXAMPLE, U.S. Pat. No. 5,562,106 to Heeke et al. teaches a non-surgical oral appliance for improving breathing, and abating or completely alleviating snoring sounds and symptoms while sleeping. The patient is pre-tested and pre-fitted for the appliance so that the appliance positions the mandible in an open position and protrusive position to hold the mouth partially open. The appliance has a right and left extension wherein each extension has upper and lower surfaces premolded to the contour of the patient's back teeth. A bridge connects the right and left extensions having been premolded to conform to the upper palate of the patient's mouth. The upper and lower surfaces of each extension are spaced to provide optimum mouth height that was pre-tested to alleviate the snoring sound. Upon insertion, the appliance facilitates an air passage for breathing and also allows the patient to talk while remaining virtually invisible to an observer.

It is apparent that numerous innovations for mouthpieces have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide a flexible retentive bite block and fabrication process that avoids the disadvantages of the prior art.

ANOTHER OBJECT of the present invention is to provide a flexible retentive bite block and fabrication process that is simple and inexpensive to manufacture.

STILL ANOTHER OBJECT of the present invention is to provide a flexible retentive bite block and fabrication process that is simple to use.

BRIEFLY STATED, YET ANOTHER OBJECT of the present invention is to provide a dentally retained intra-oral appliance worn at night for treatment of snoring and obstructive sleep apnea and its fabrication process. The appliance maintains the patient's mandible in an anterior, protruded position to prevent obstruction of the pharyngeal airway. The appliance allows a limited degree of lateral movement of the mandible relative to the upper jaw in the protruded position to prevent aggravation of the patient's temporomandibular joint and associated muscles and ligaments. The appliance includes a lower bite block conforming to the patient's mandibular dentition, an upper bite block conforming to the patient's maxillary dentition, and a hinge connecting the upper bite block to the lower bite block. The upper bite block and the lower bite block are thin walled polyamide eliminating the need for dental wires to maintain them to the mandibular detention and the maxillary dentition and the problems associated therewith.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures on the drawing are briefly described as follows:

FIG. 8 is an exploded diagrammatic perspective view of steps 81 and 82 of the process of the present invention, and also shows the final assemblage of the article of manufacture the flexible retentive bite blocks of present invention produced by the fabrication process of the present invention.

Figure 1:
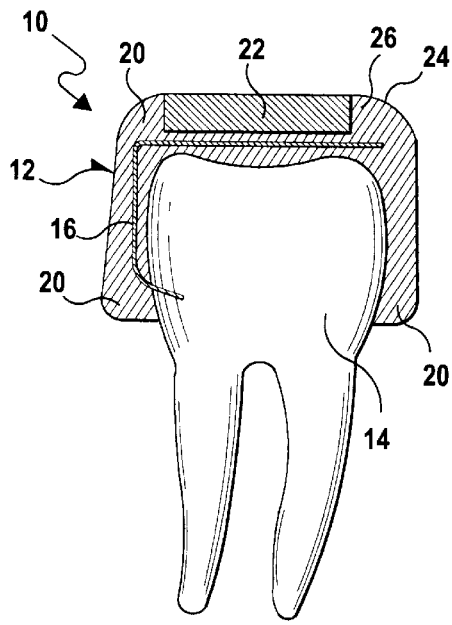
FIG. 1 is a diagrammatic side elevational view, in partial cross sectional, of a prior art bite block taught by U.S. Pat. No. 5,365,945 to Halstrom, installed on a patient's teeth.
Figure 2:
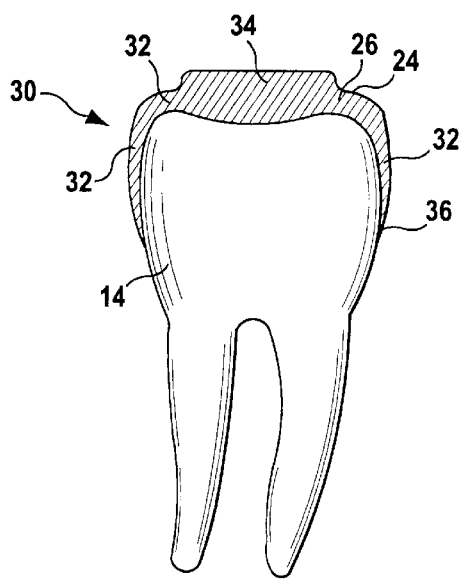
FIG. 2 is a diagrammatic side elevational view, in partial cross sectional, of the apparatus of the present invention installed on a patient's teeth.

LIST OF REFERENCE NUMERALS UTILIZED
IN THE DRAWING

Prior Art 10 appliance
12 lower bite block
14 patient's mandibular dentition
16 dental wires
20 walls of appliance 10
22 pair of opposing bite pads
24 biting surfaces 24 of posterior portions 26
26 posterior portions Present Invention 30 flexible retention bite block
32 walls
34 pair of opposing bite pads
36 supra bulge of mandibular detention 14
38 lower duplicate casting
40 gum of lower duplicate casting 38
42 teeth of lower duplicate casting 38
44 cross section of mounting surface of articulator with parts broken away
46 surveying line of teeth 42 of lower duplicate casting 38
48 extended surveying line of teeth 42 of lower duplicate casting 38
50 heat pressure former
52 at least one plastic spacer sheet
54 conformed plastic spacer layer on lower duplicate casting 38
56 pair of opposing metal bite pads on conformed plastic spacer layer 54 on lower duplicate casting 38
57 lower pattern
58 lower processing stylus
60 guide box
62 narrow stub portion of lower processing stylus 58
64 base plate
66 processing screws
67 lower assemblage
68 upper duplicate casting
70 gum of upper duplicate casting 68
72 teeth of upper duplicate casting 68
74 supra bulges of teeth 72 of upper duplicate casting 68
76 surveying line of upper duplicate casting 68
78 extended surveying line of upper duplicate casting 68
80 at least one plastic spacer sheet
82 conformed plastic spacer layer on upper duplicate casting 68
84 pair of opposing metal bite pads on conformed plastic spacer layer 82 on upper duplicate casting 68
85 upper pattern
86 retention plate
88 aperture in retention plate 86
90 part of upper processing jig 92
92 upper processing jig
94 non-threaded portion 94 of final stylus 96
96 final stylus
98 threaded portion 98 of final stylus 96
100 upper assemblage
102 stone
103 upper bite block
104 lower portion 104 of flask 106
105 lower bite block
106 flask
108 upper portion of flask 106
110 wax sprue on upper assemblage 100
112 wax sprue on lower assemblage 67
113 pair of permanent screws
114 head of lower processing stylus 58
116 milled-out cavity in guide box 60
118 shaft of lower processing stylus 58
120 kidney-shaped aperture in upper surface 122 of guide box 60
122 upper surface of guide box 60
124 head of each of processing screws 66
126 shaft of each of processing screws 66
128 three non-threaded apertures 122 in base plate 64
130 stub portion of each of processing screws 66
132 pair of threaded apertures 126 in guide box 60
134 shaft of each of processing screws 66
136 base of processing jig 92
138 center portion of base 36 of processing jig 92
140 aperture in center portion 138 of base 36 of processing jig 92
142 pair of opposing wing portions of base 36 of processing jig 92
144 plurality of stub portions of processing jig 92
146 head of final stylus 96
148 head of each of pair of permanent screws 113
150 shaft of each of pair of permanent screws 113
152 stub portion of each of pair of permanent screws 113

DETAILED DESCRIPTION OF THE
PREFERRED EMBODIMENT

The fabrication process of the flexible retentive bite block 30 can best be seen in FIGS. 3 through 9MM inclusive, and as such will be discussed with reference thereto.

STEP 1: Make a optional duplicate of an original lower casting forming a lower duplicate casting 38 having a gum 40, teeth 42 with the supra bulges 36 and posterior portions with bite surfaces.

STEP 2: Mount the lower duplicate casting 38 on an articulator 44.

Figure 3:
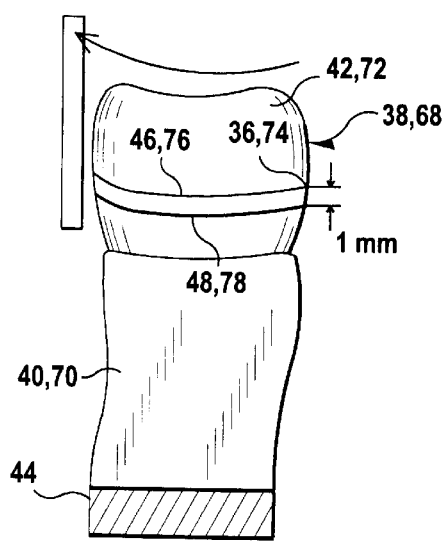
FIG. 3 is a diagrammatic side elevational view illustrating the step of surveying a tooth of the model as further illustrated by steps 3, 4, 17 and 18 of the fabrication process of the present invention.

STEP 3: As shown in FIG. 3, survey the lower duplicate casting 38 forming a surveying line 46 thereon.

STEP 4: As shown in FIG. 3, extend the surveying line 46 approximately 1 mm past the supra bulges 36 of the teeth 42 of the lower duplicate casting 38, toward the gum 40 of the lower duplicate casting 38, forming an extended surveying line 48.

STEP 5: Remove the lower duplicate casting 38 from the articulator 44.

Figure 4:
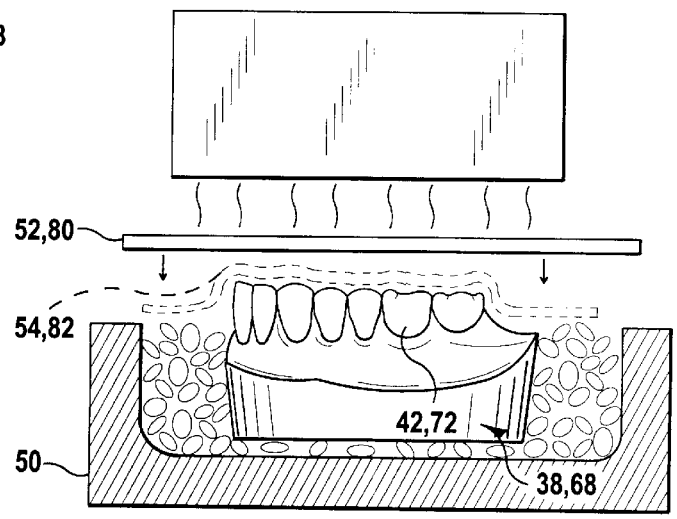
FIG. 4 is a diagrammatic side elevational view partially in section, with parts broken away, illustrating the plastic spacer layer being applied and conformed to the model as further illustrated by steps 6, 7, 8, 20, 21, and 22 of the fabrication process of the present invention.

STEP 6: As shown in FIG. 4, put the lower duplicate casting 38 in a heat pressure former 50. A typical heat pressure former 50 is sold by either ERKOPRESS or BIO-STAR.

STEP 7: As shown in FIG. 4, position at least one plastic spacer sheet 52 on the teeth 42 of the lower duplicate casting 38.

Step 8: As shown in FIG. 4, activate the heat pressure former 50 causing the at least one plastic spacer sheet 52 to melt and conform to the teeth 42 of the lower duplicate casting 38 forming a conformed plastic spacer layer 54 thereon.

STEP 9: Remove the lower duplicate casting 38 with the conformed plastic spacer layer 54 thereon from the heat pressure former 50.

Figure 5:
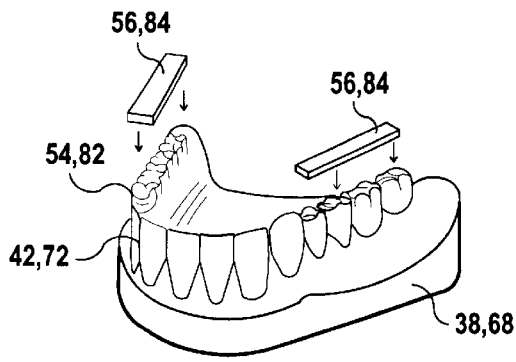
FIG. 5 is a diagrammatic perspective view illustrating a metal bite pads about to be attached to the model with luting agent as further illustrated by steps 10 and 24 of the fabrication process of the present invention.

STEP 10: As shown in FIG. 5, affix a pair of opposing metal bite pads 56 on the conformed plastic spacer layer 54, at the bite surfaces of the posterior portions of the teeth 42 of the lower duplicate casting 38, utilizing a wax luting agent, and forming therewith a lower pattern 57 (see FIG. 6).

STEP 11: Replace the lower duplicate casting 38 with the lower pattern 57 thereon on the articulator 44.

Figure 6:
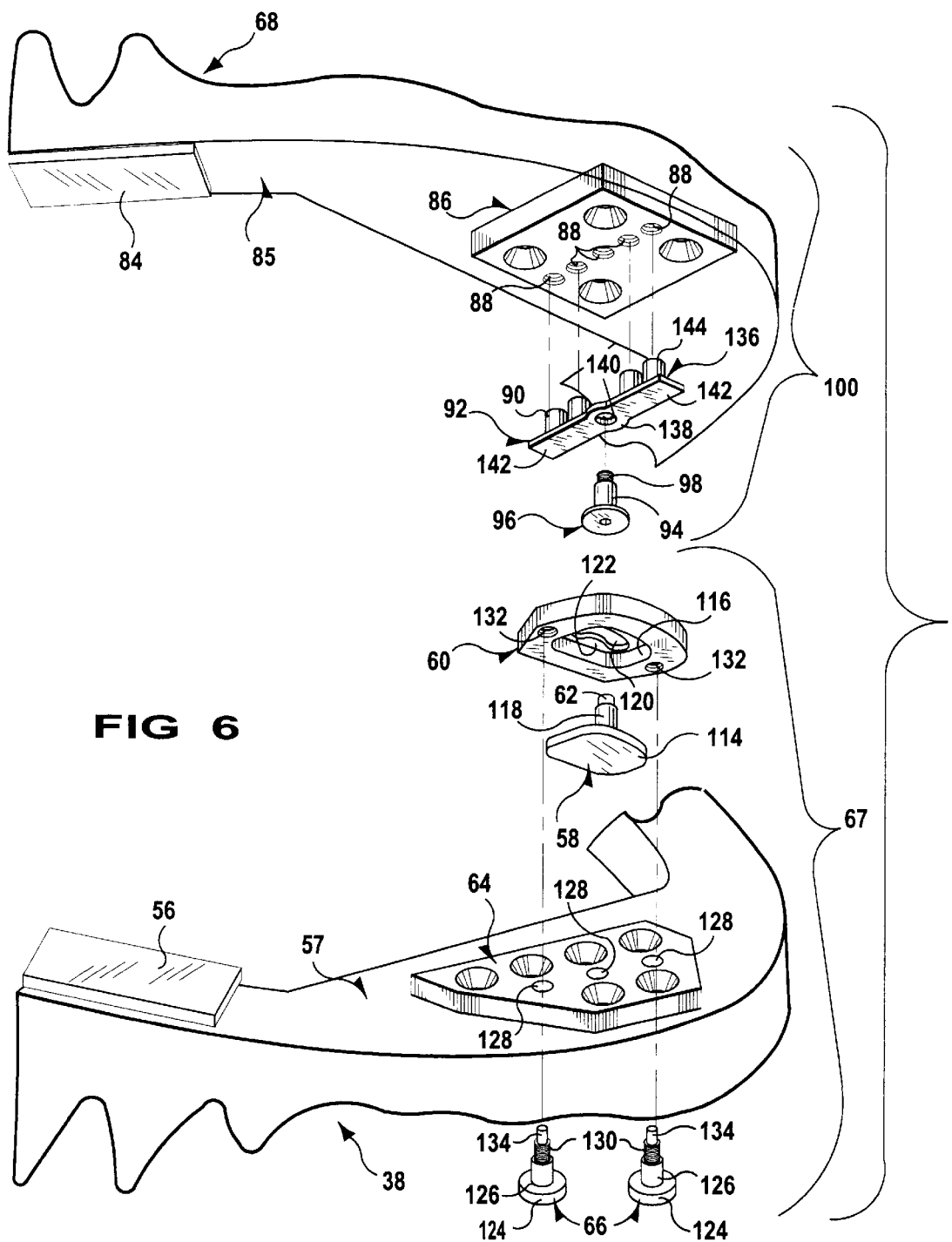
FIG. 6 is an exploded diagrammatic perspective view illustrating various components utilized in the fabricating of the upper and lower bite blocks with their typical relative locations to each other as further illustrated by steps 12, 13, 14, 26, 27, 28 and 29 of the fabrication process of the present invention.
Figure 9A:
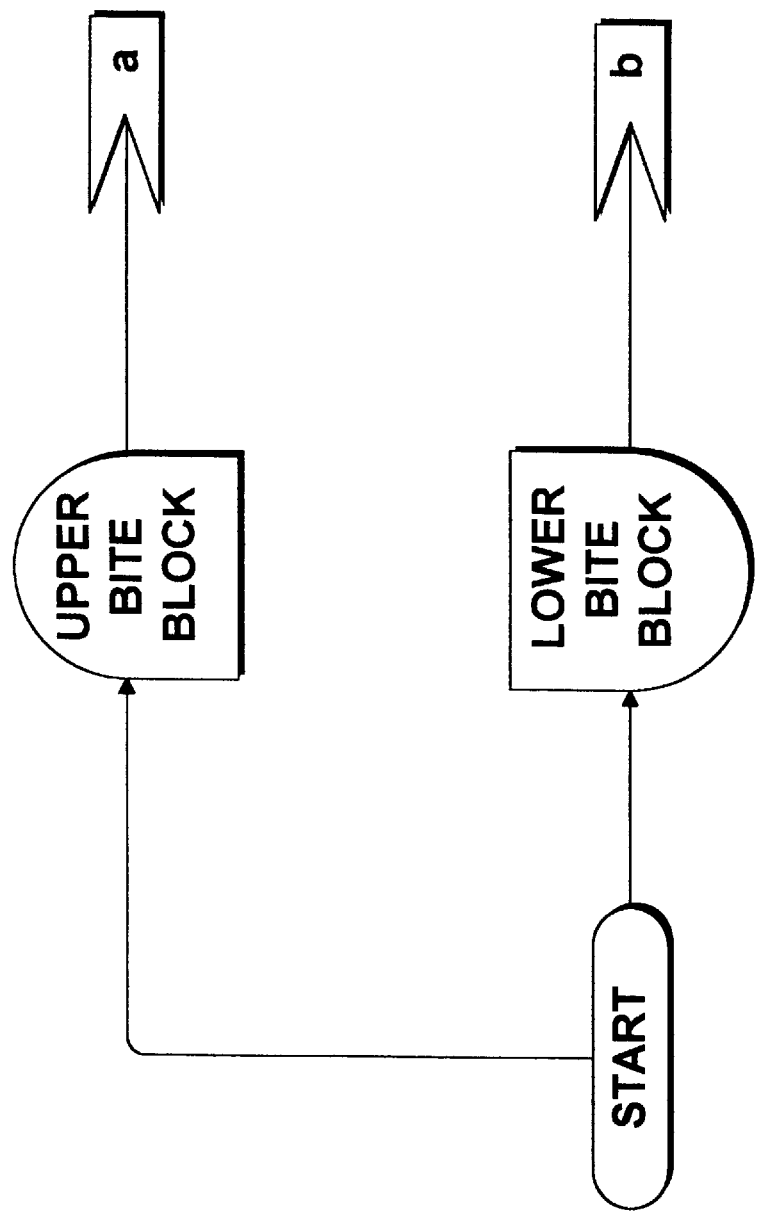
FIGS. 9A–9MM is a process flow diagram for carrying out the fabrication process of the present invention.
Figure 9B:
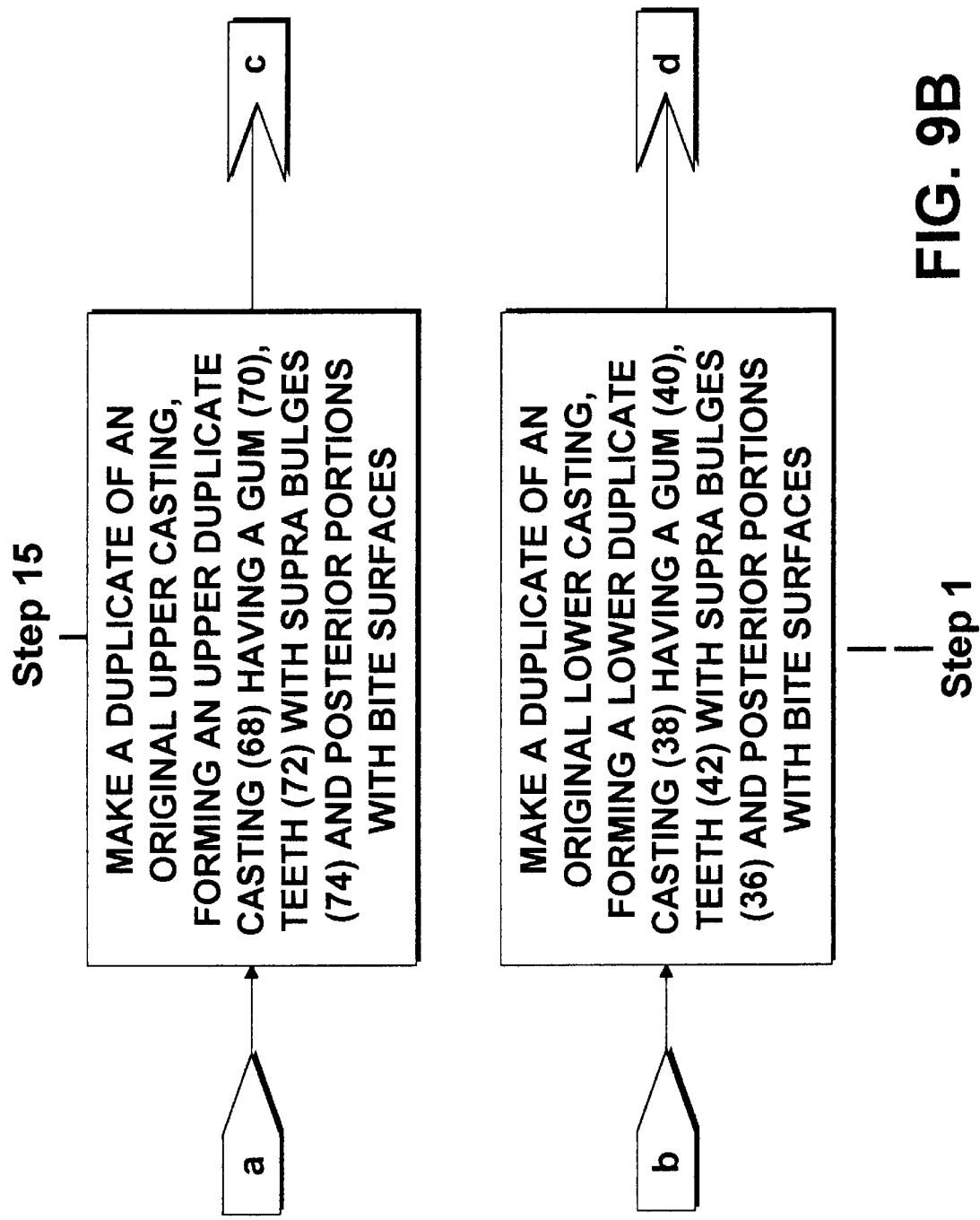
Figure 9F:
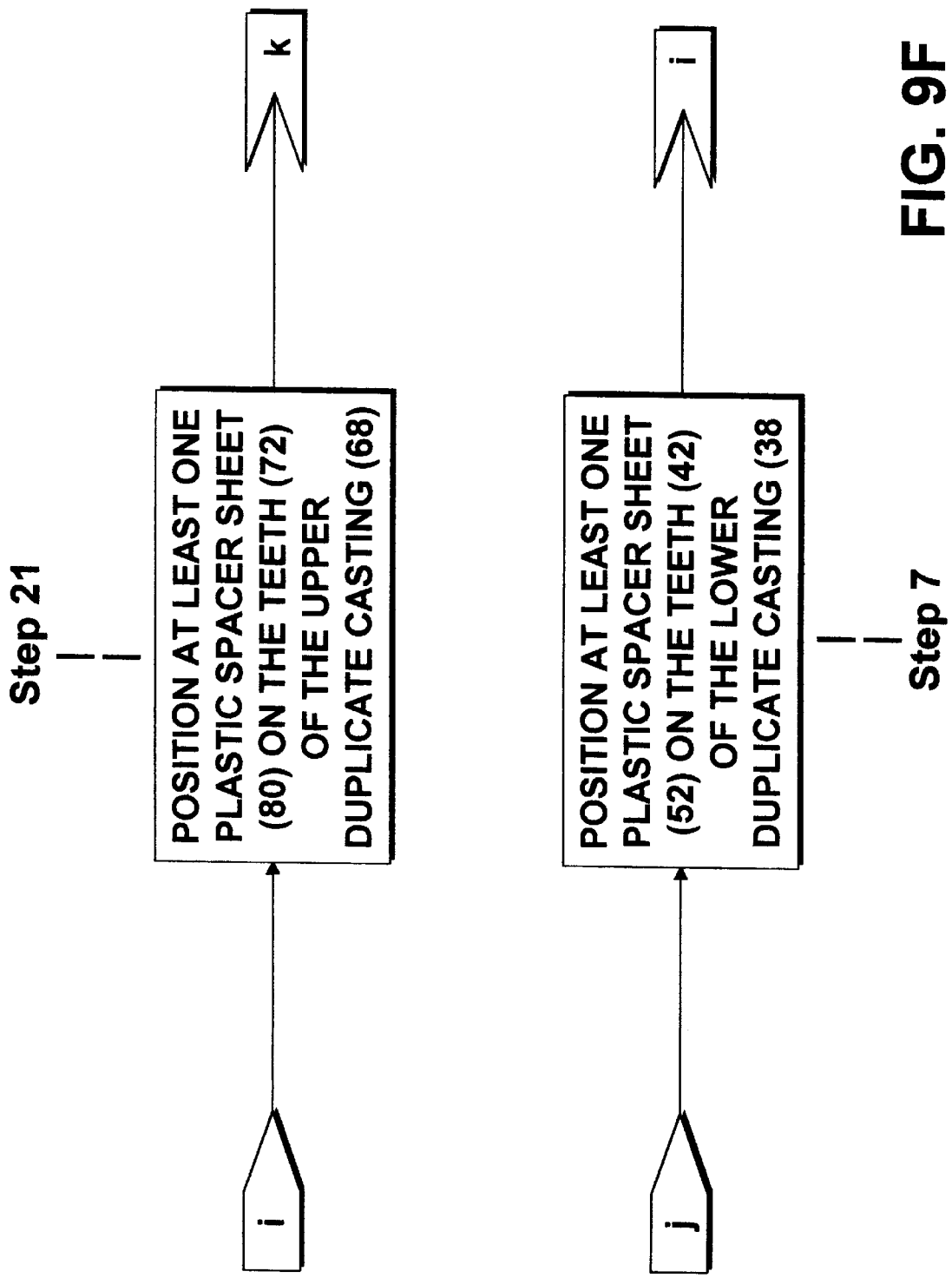
Figure 9H:
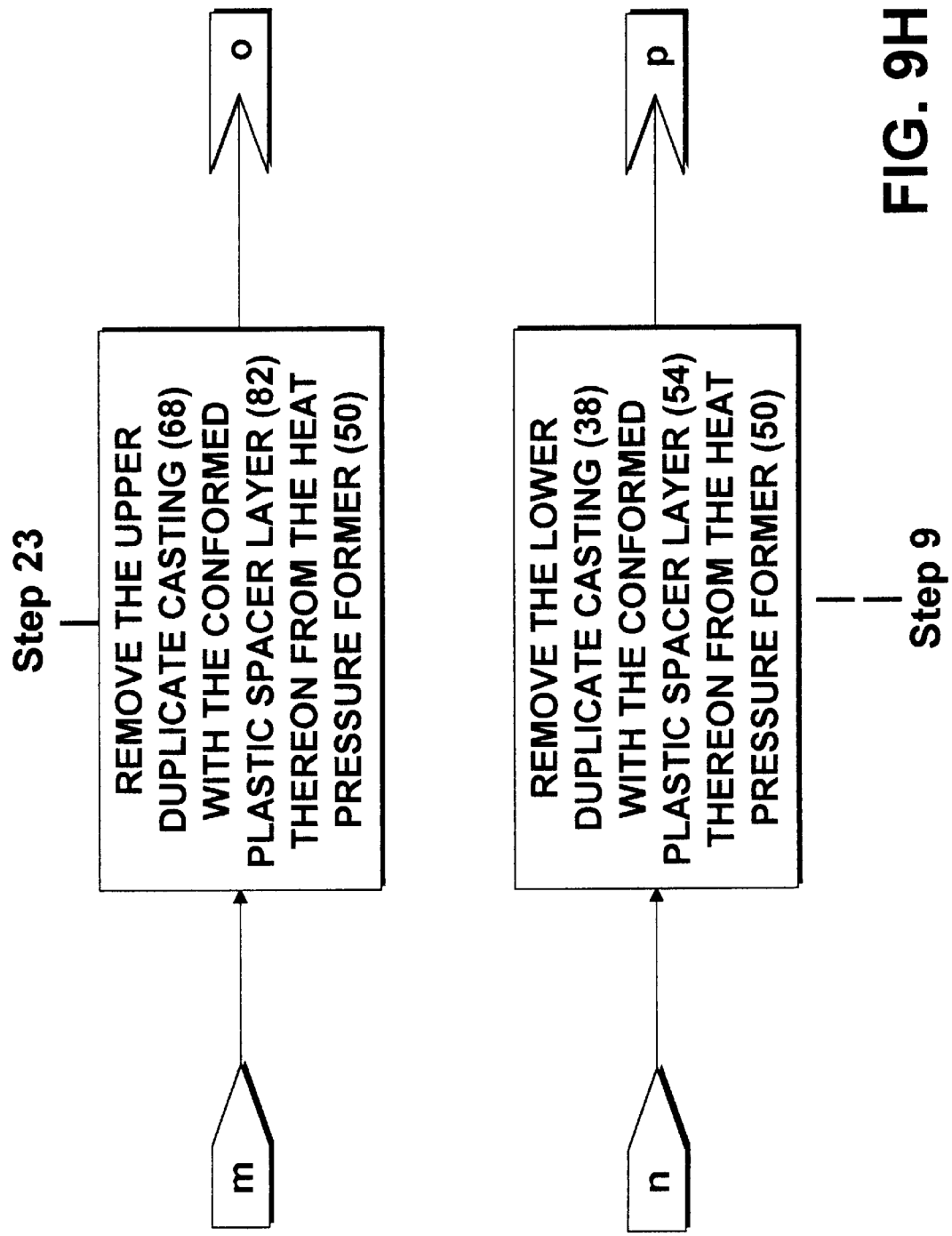
Figure 9I:
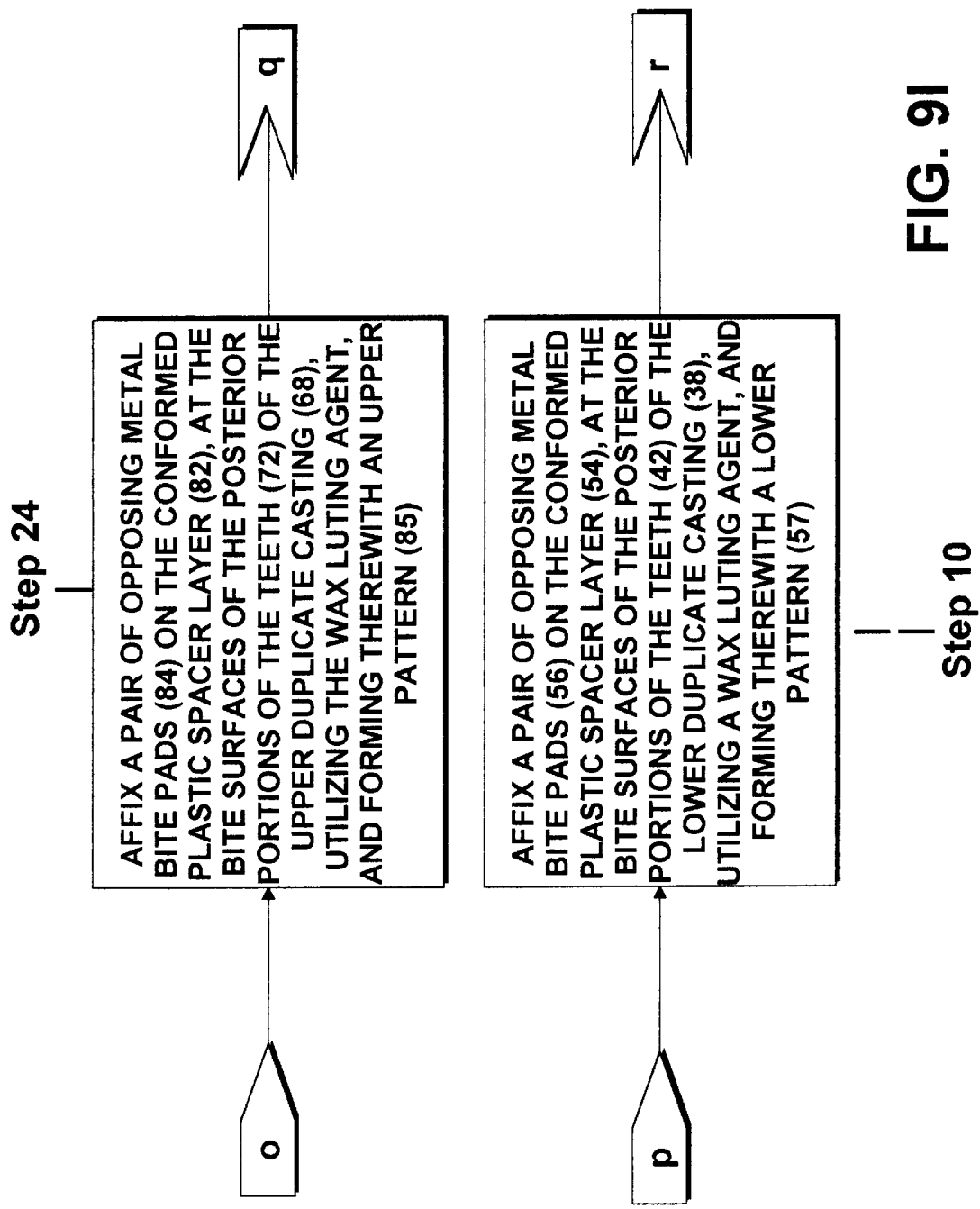
Figure 9K:
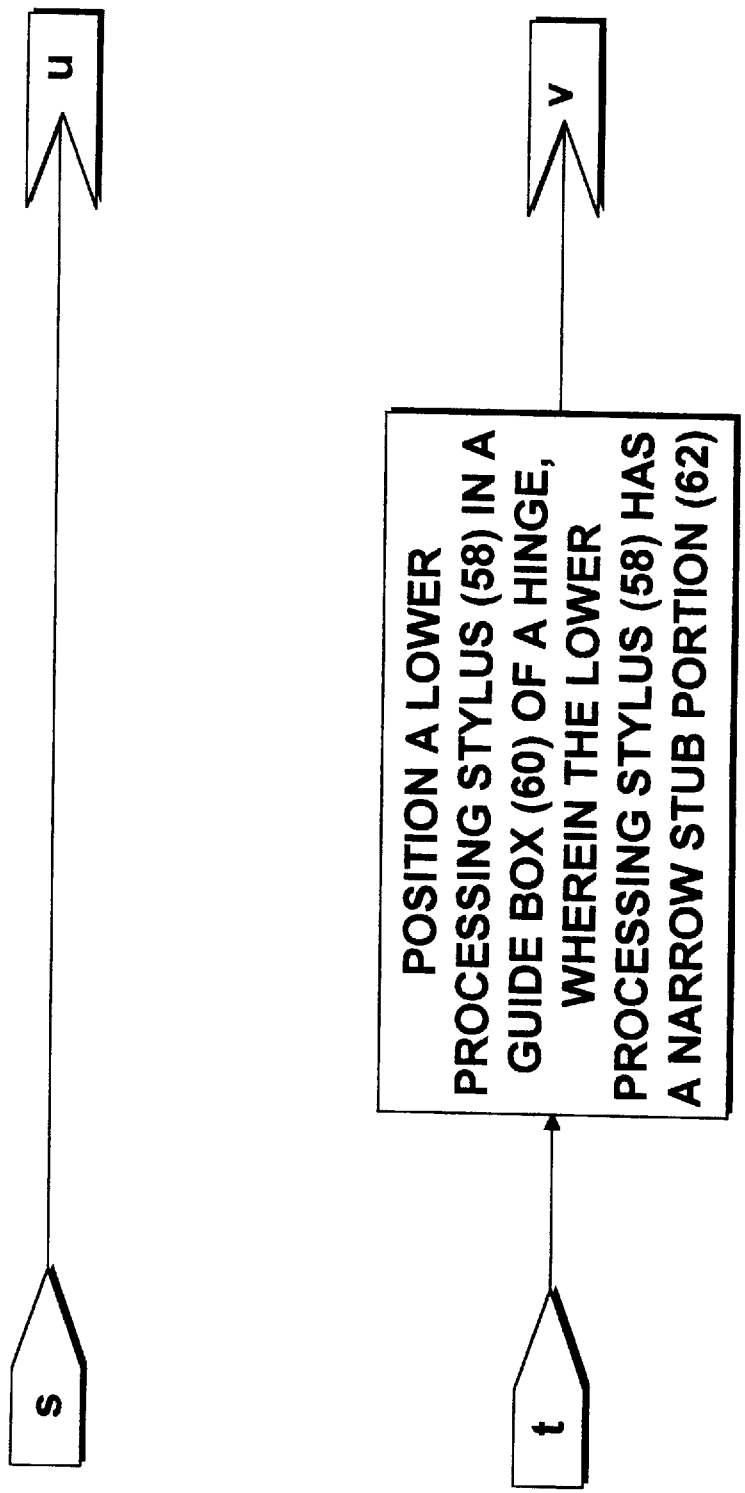
Figure 9M:
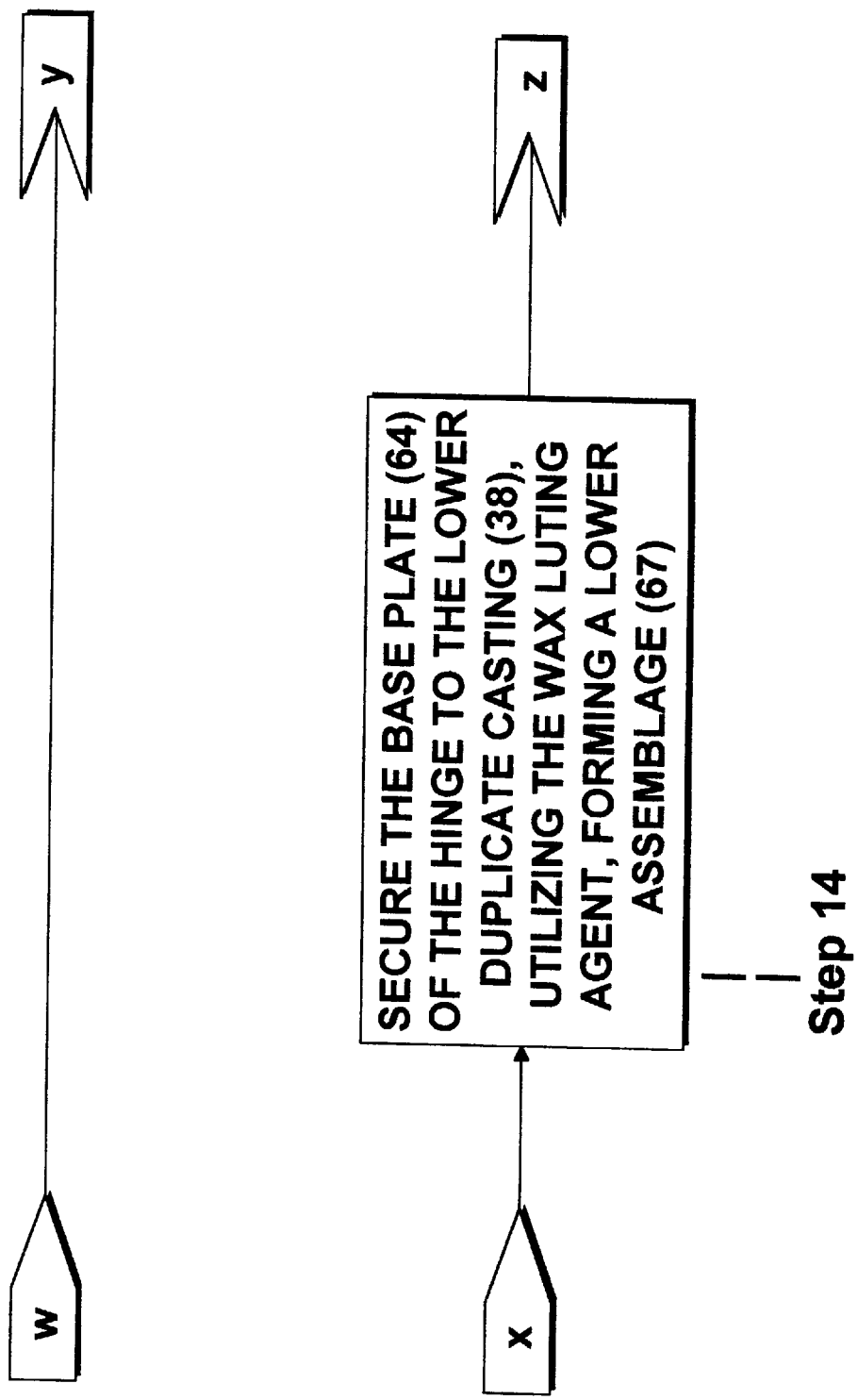
Figure 9N:
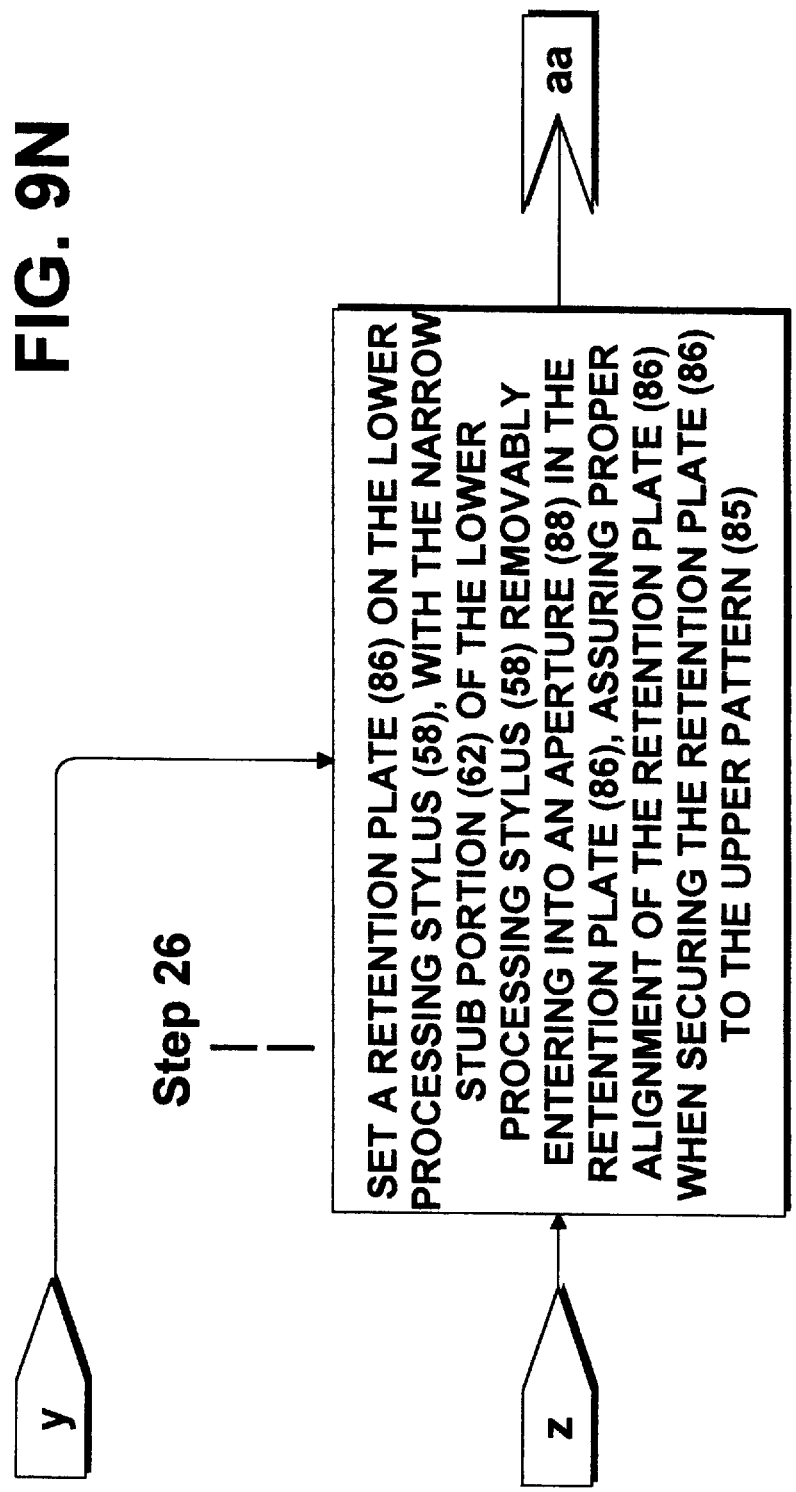
Figure 9P:
Figure 9R:
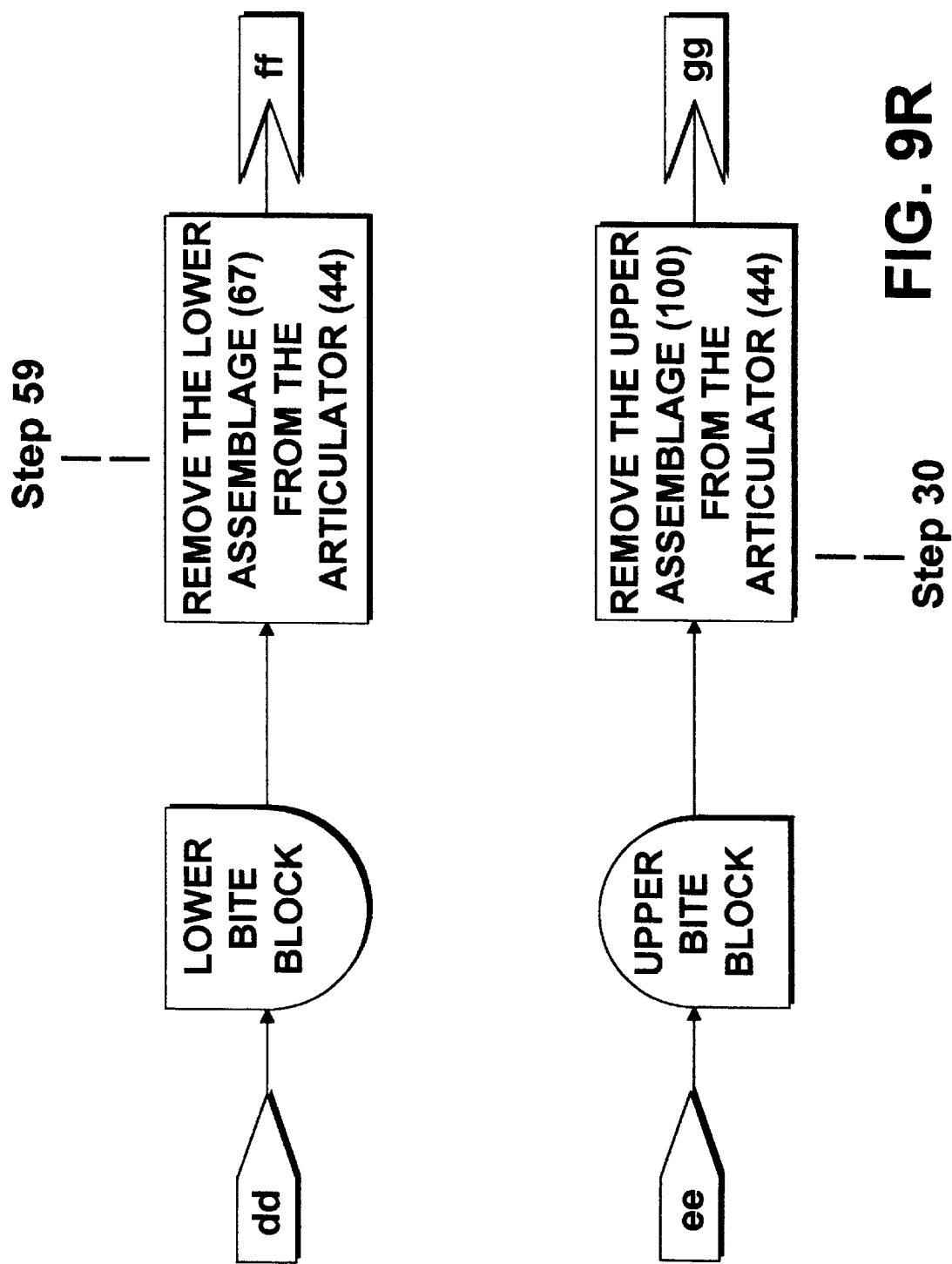
Figure 9S:
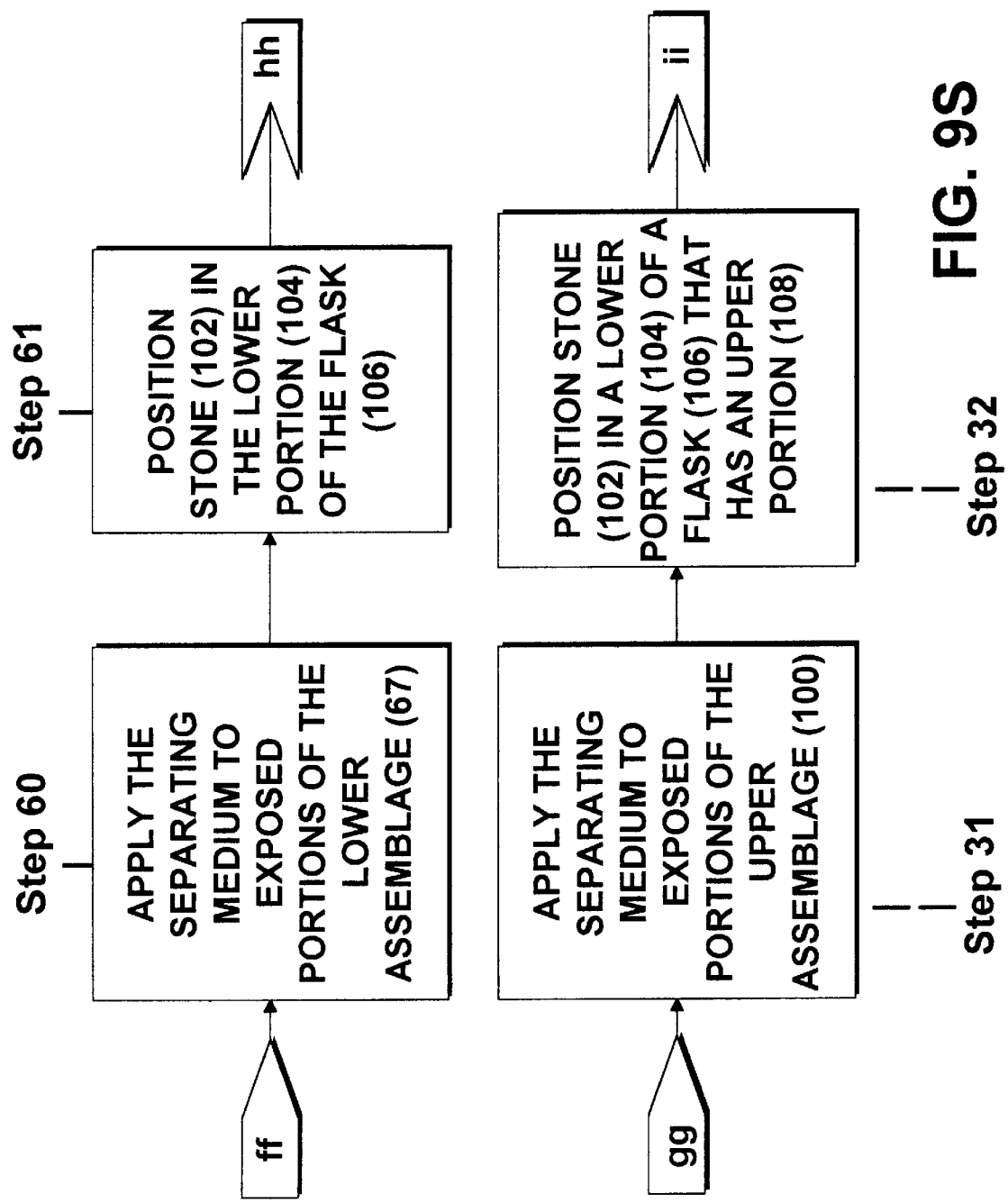
Figure 9T:
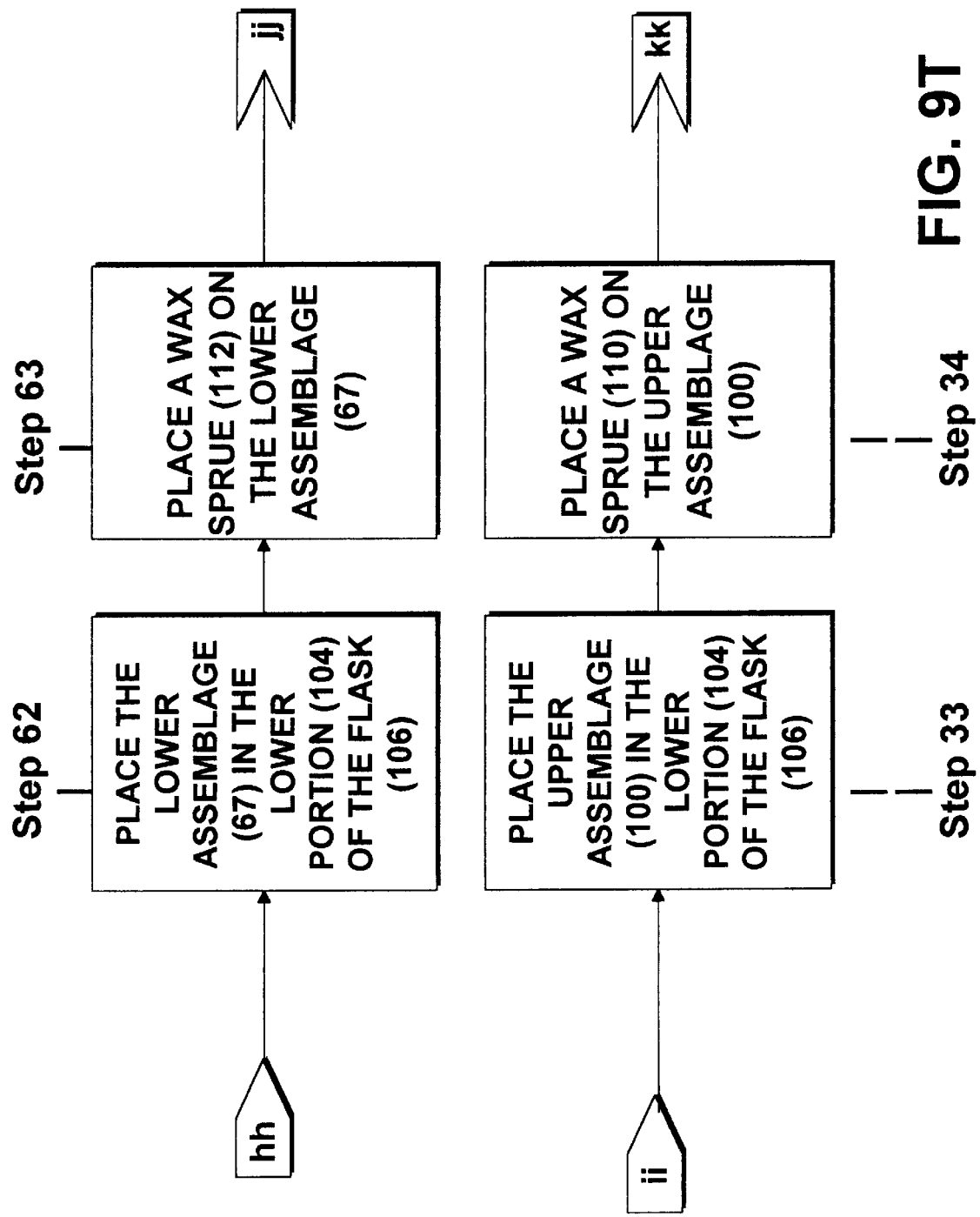
Figure 9W:
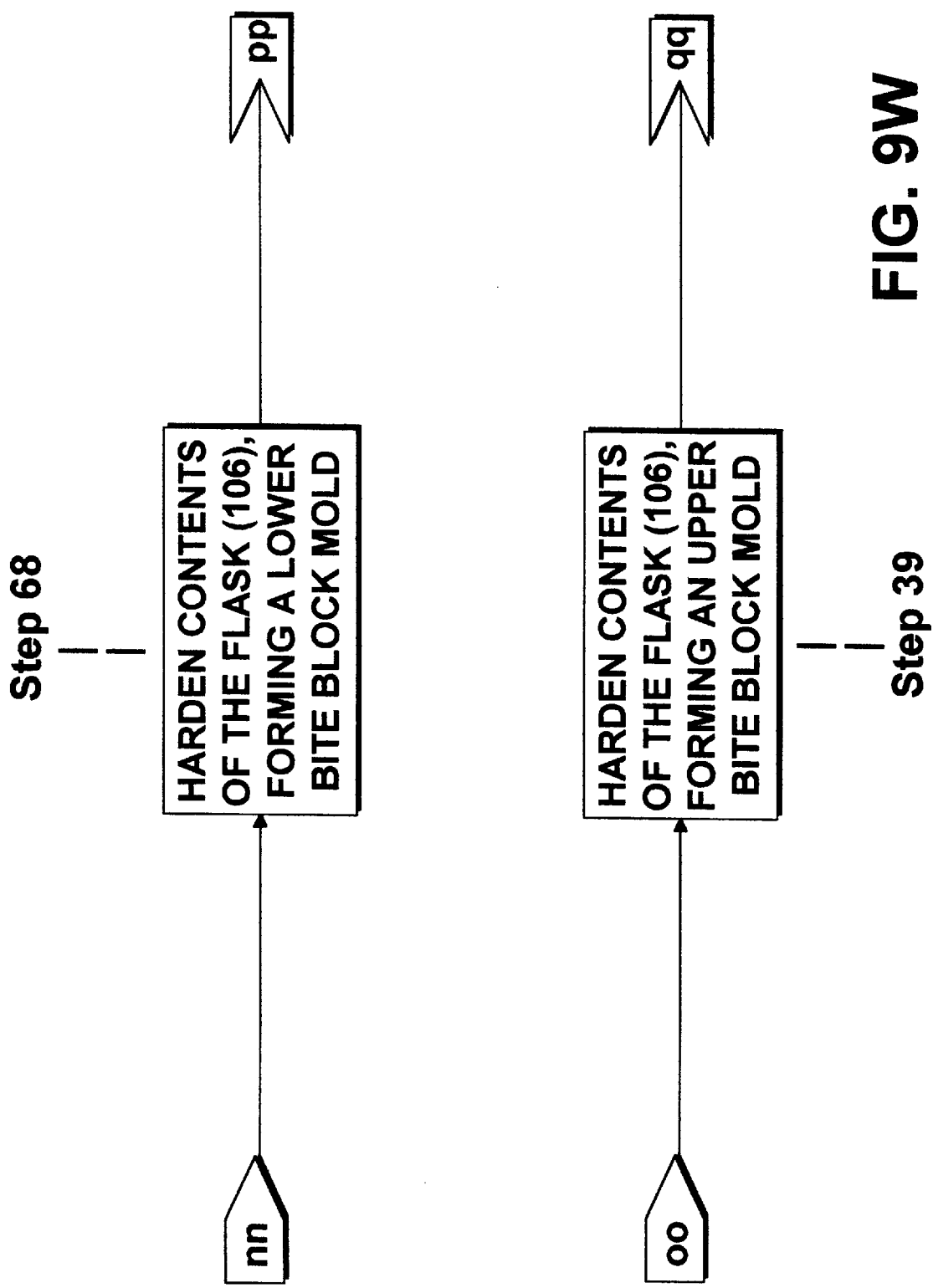
Figure 9X:
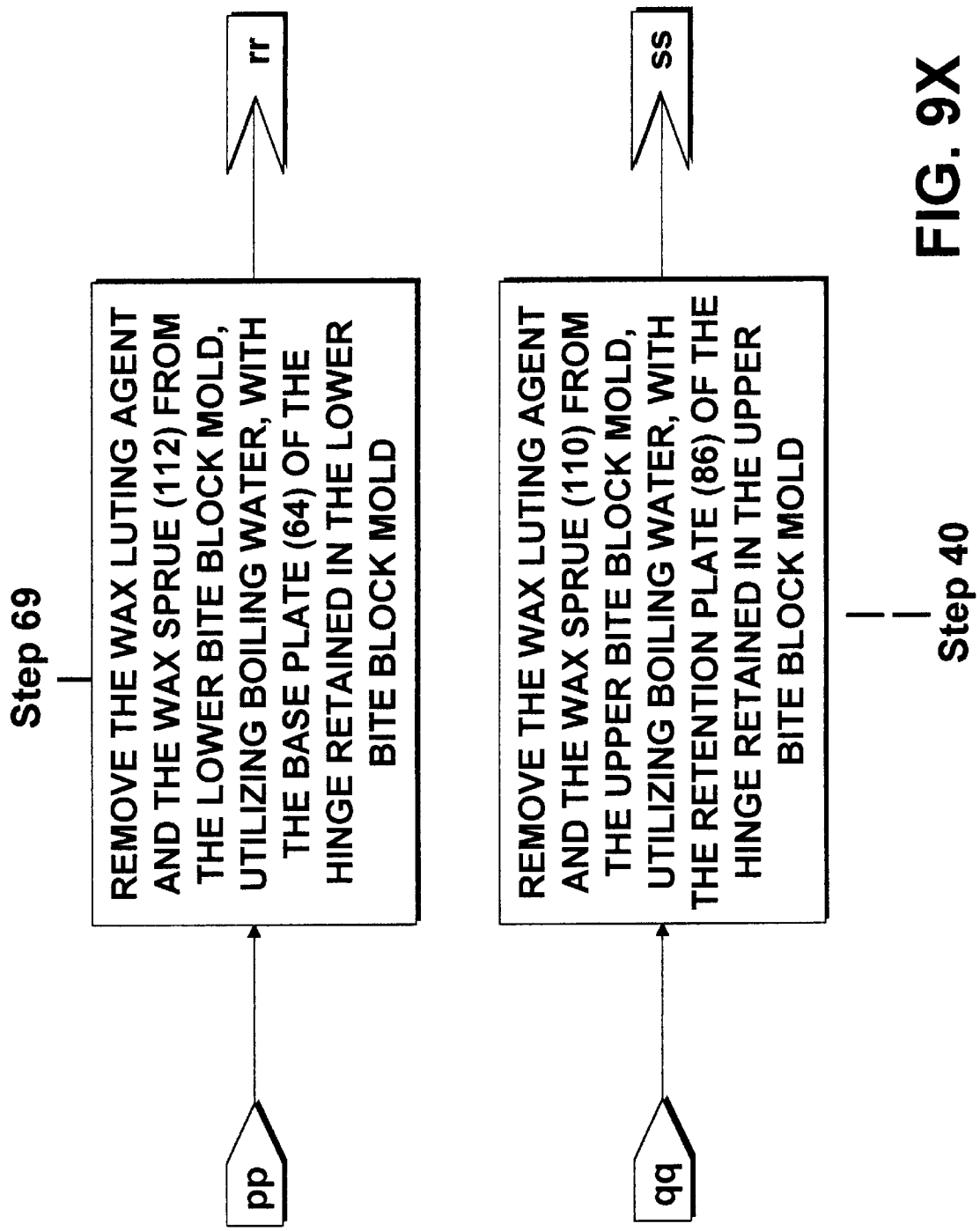
Figure 9Y:
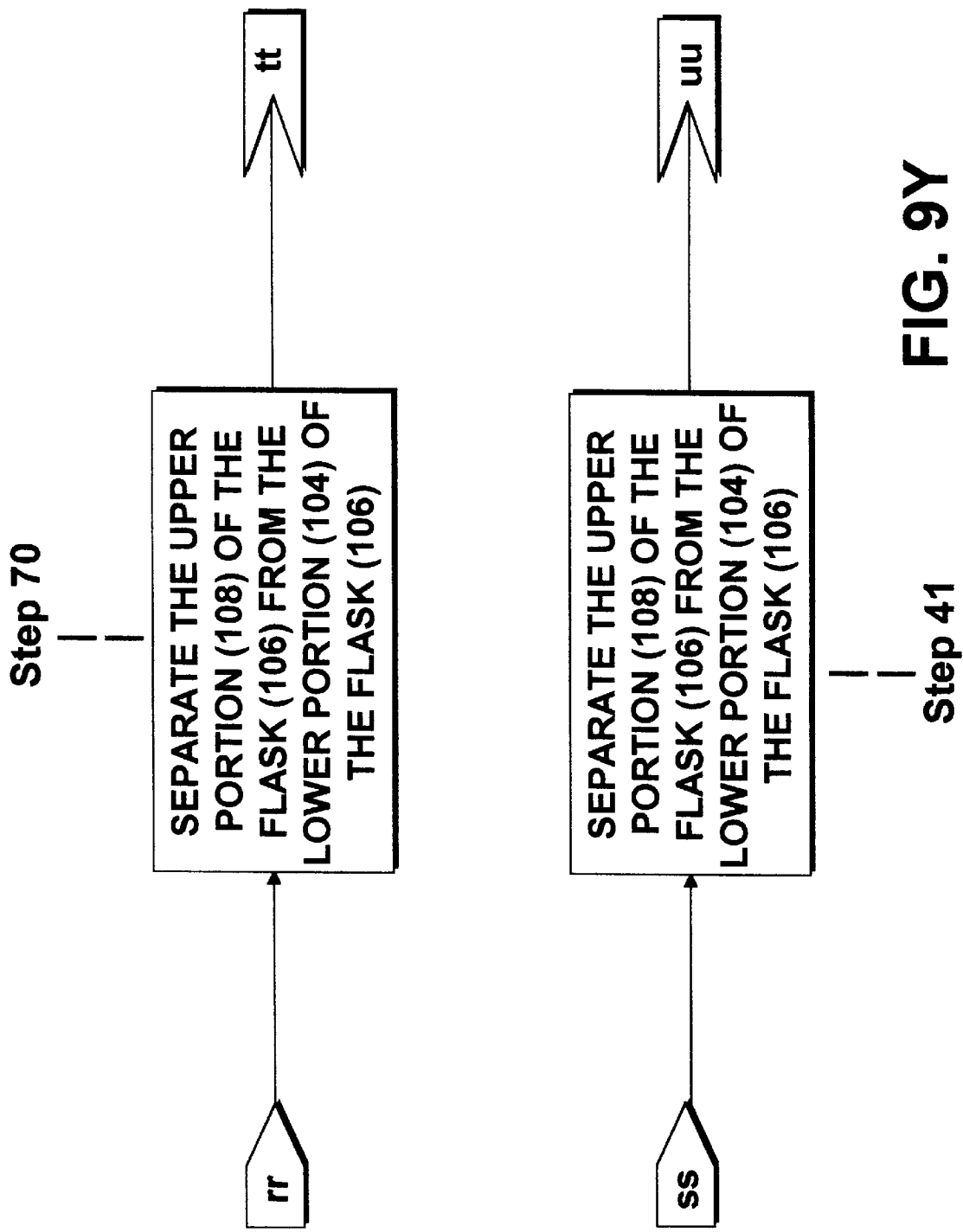
Figure 9A:
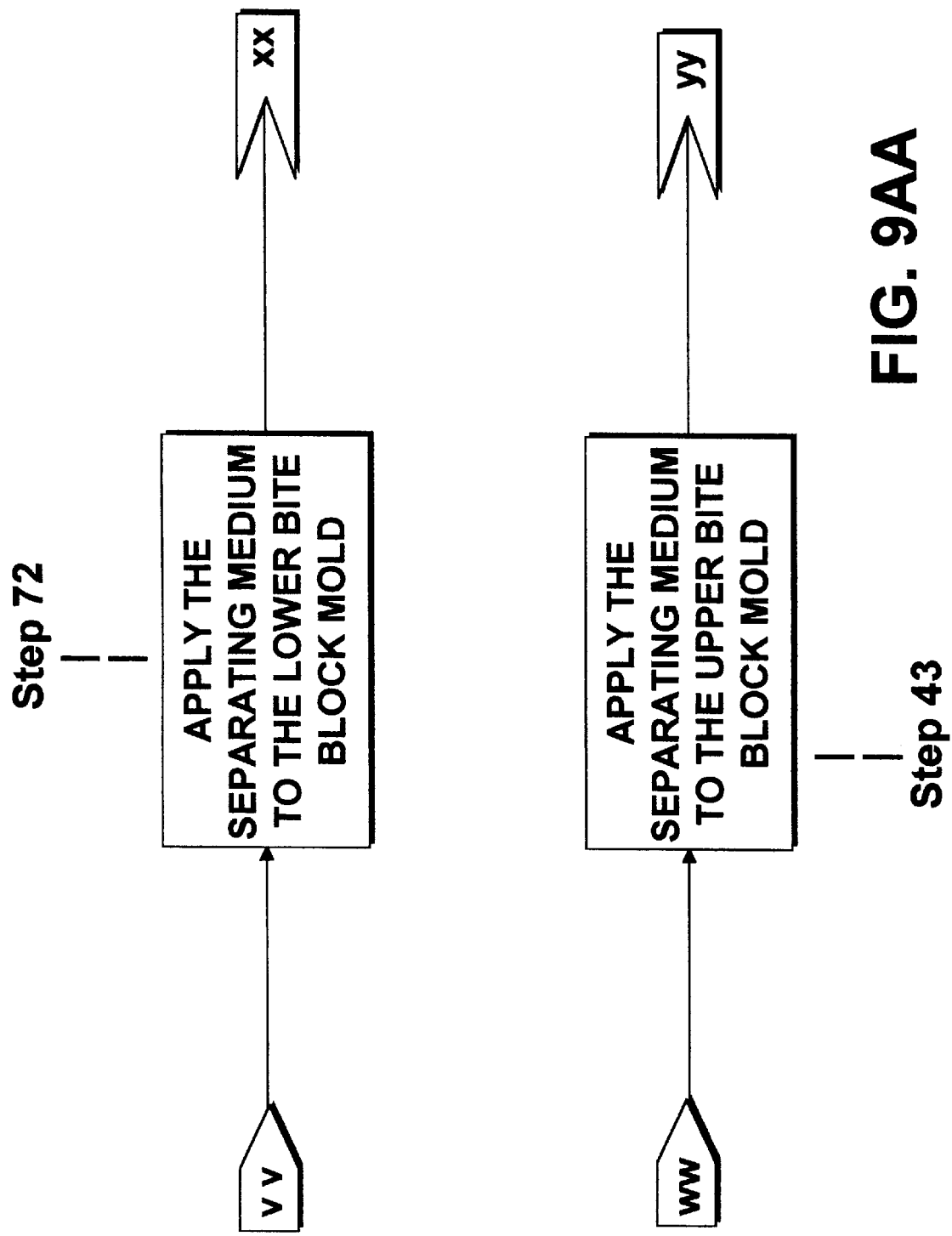
Figure 9B:
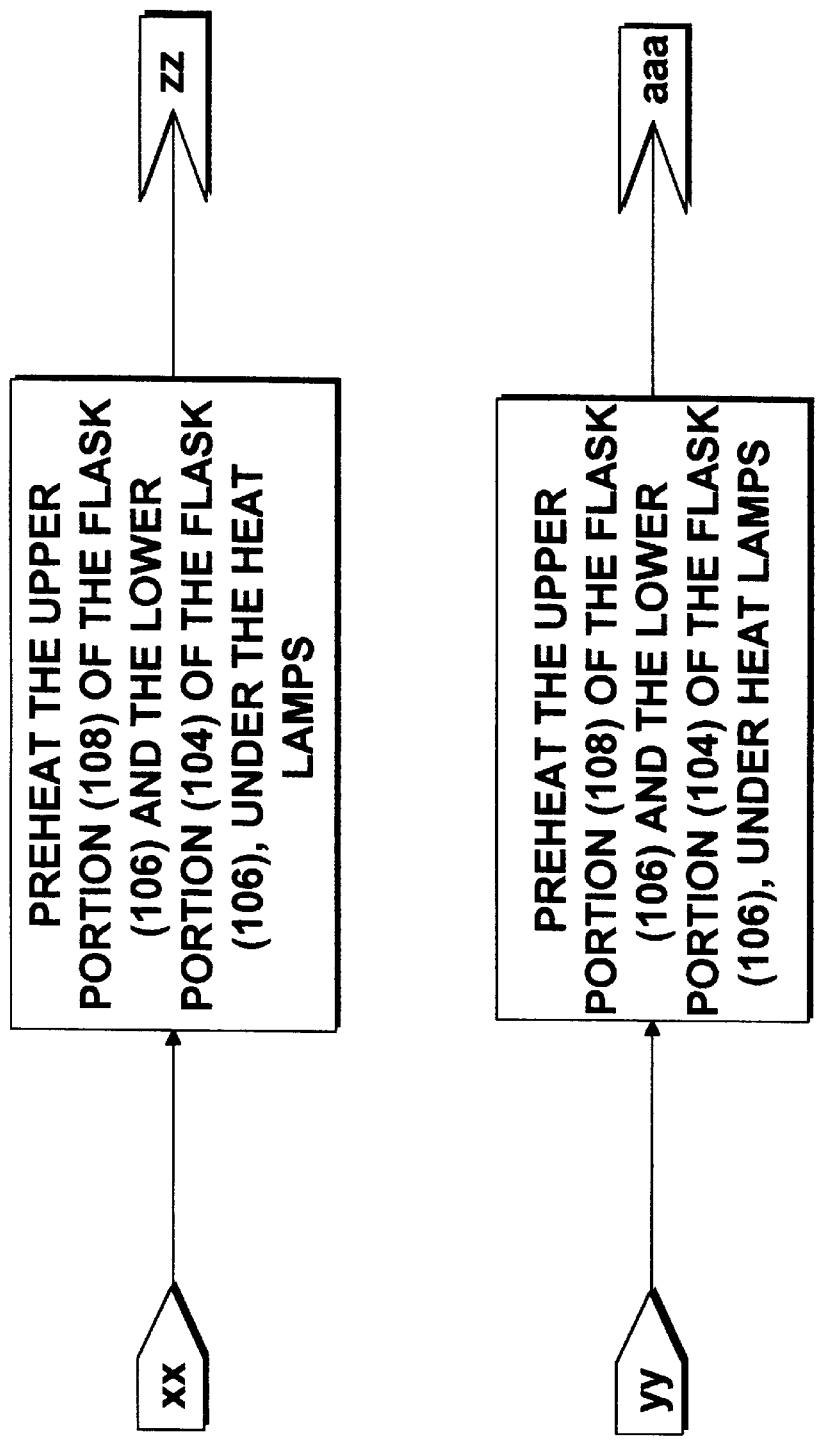
Figure 9D:
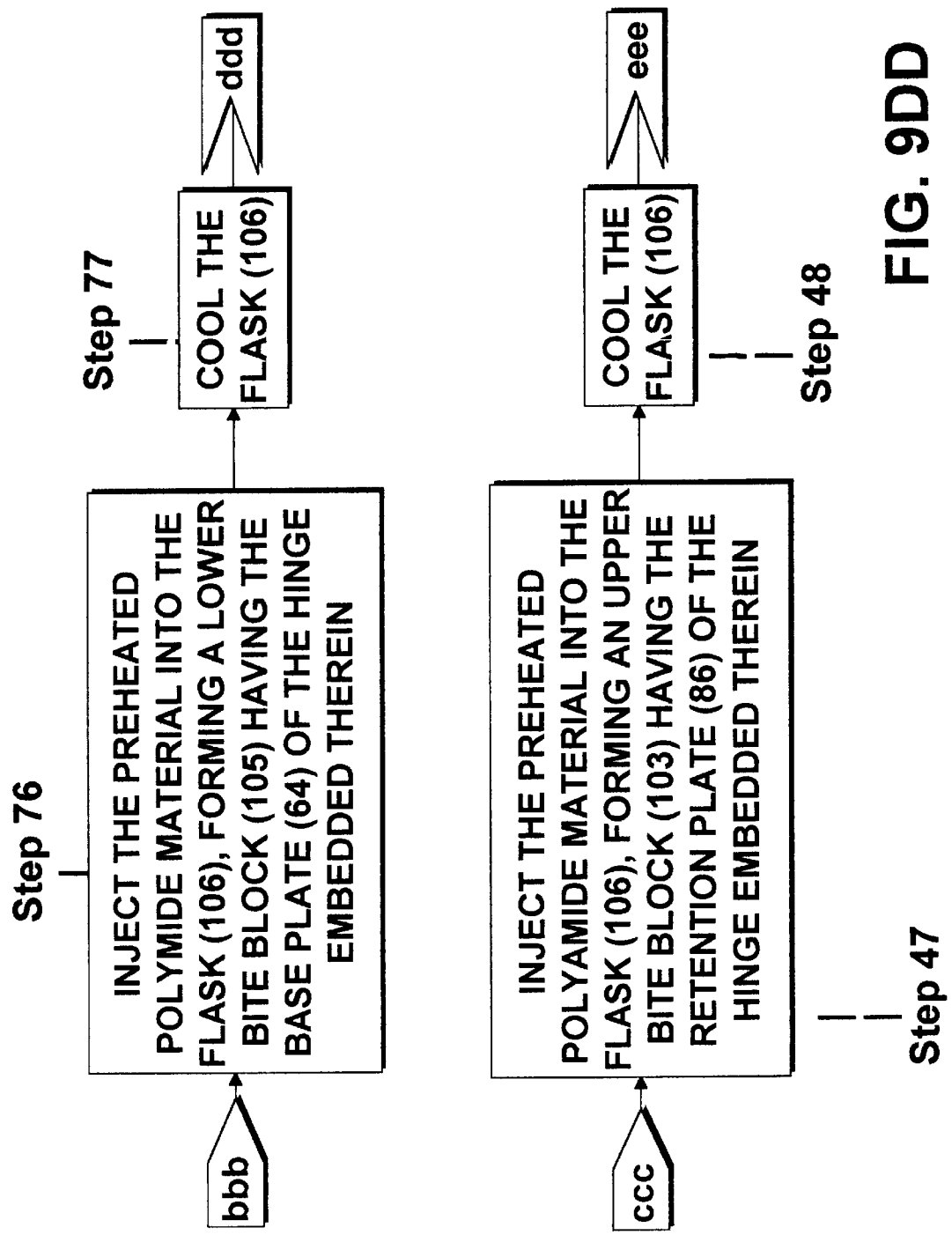
Figure 9E:
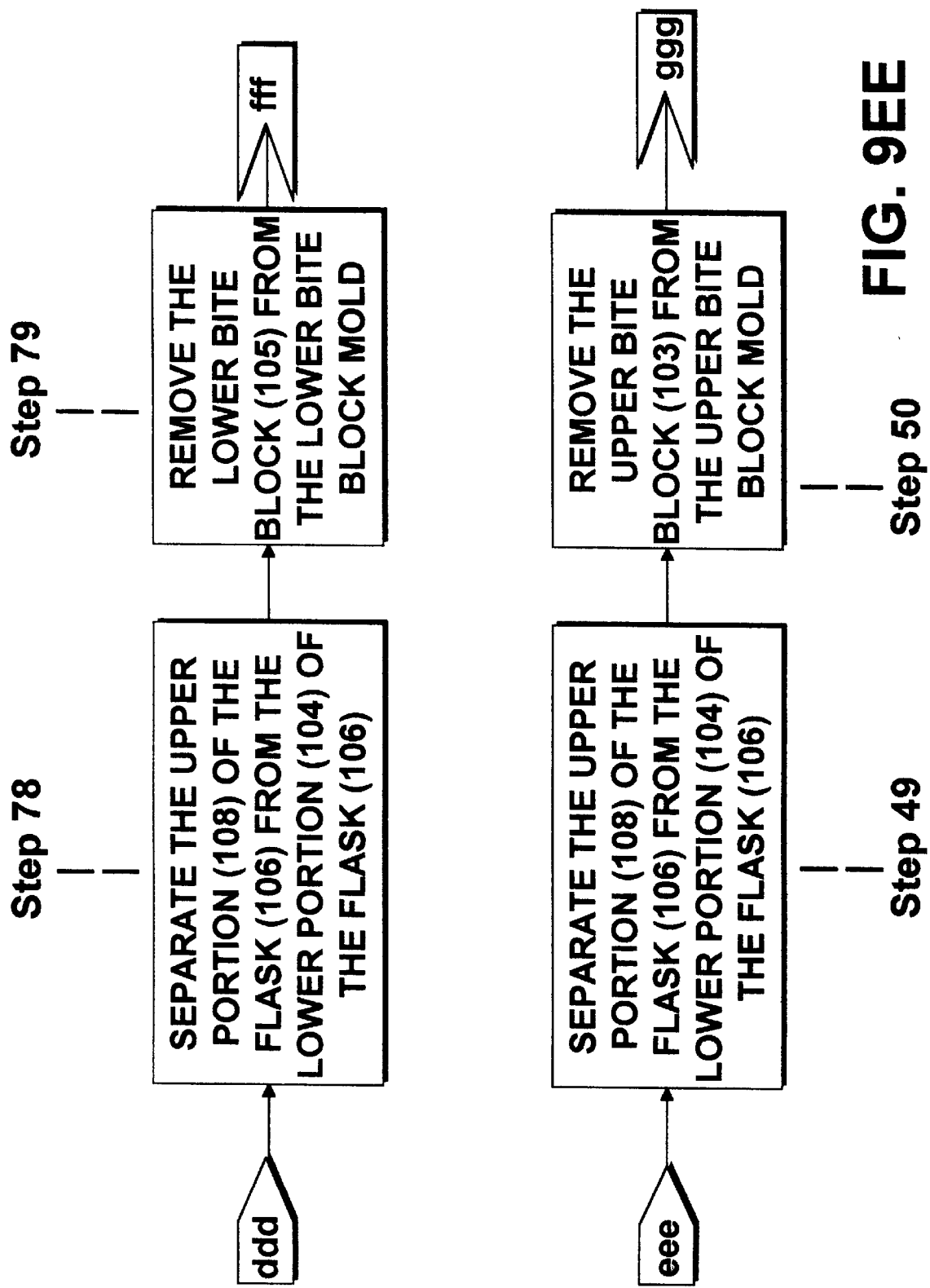
Figure 9F:
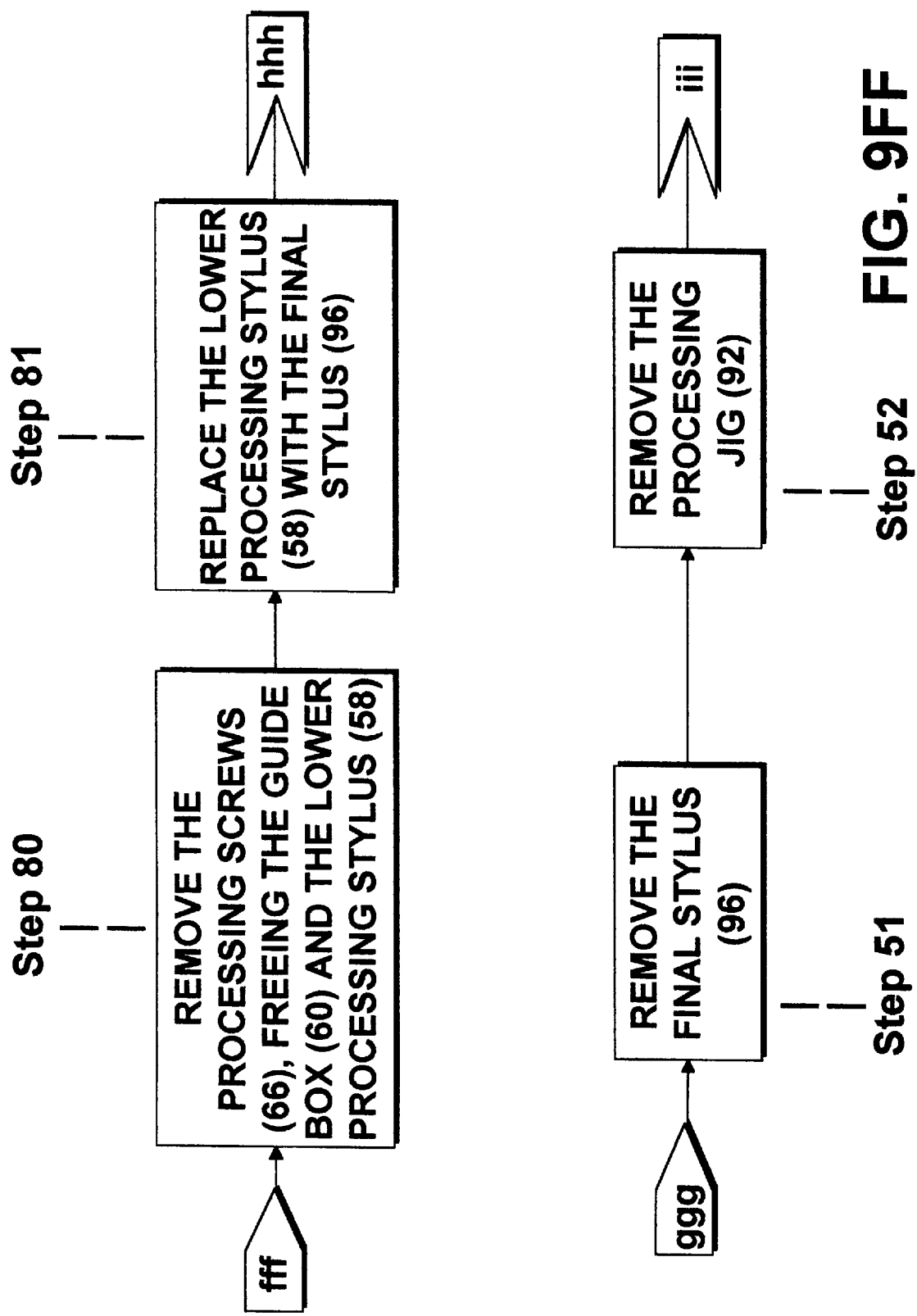
Figure 9G:
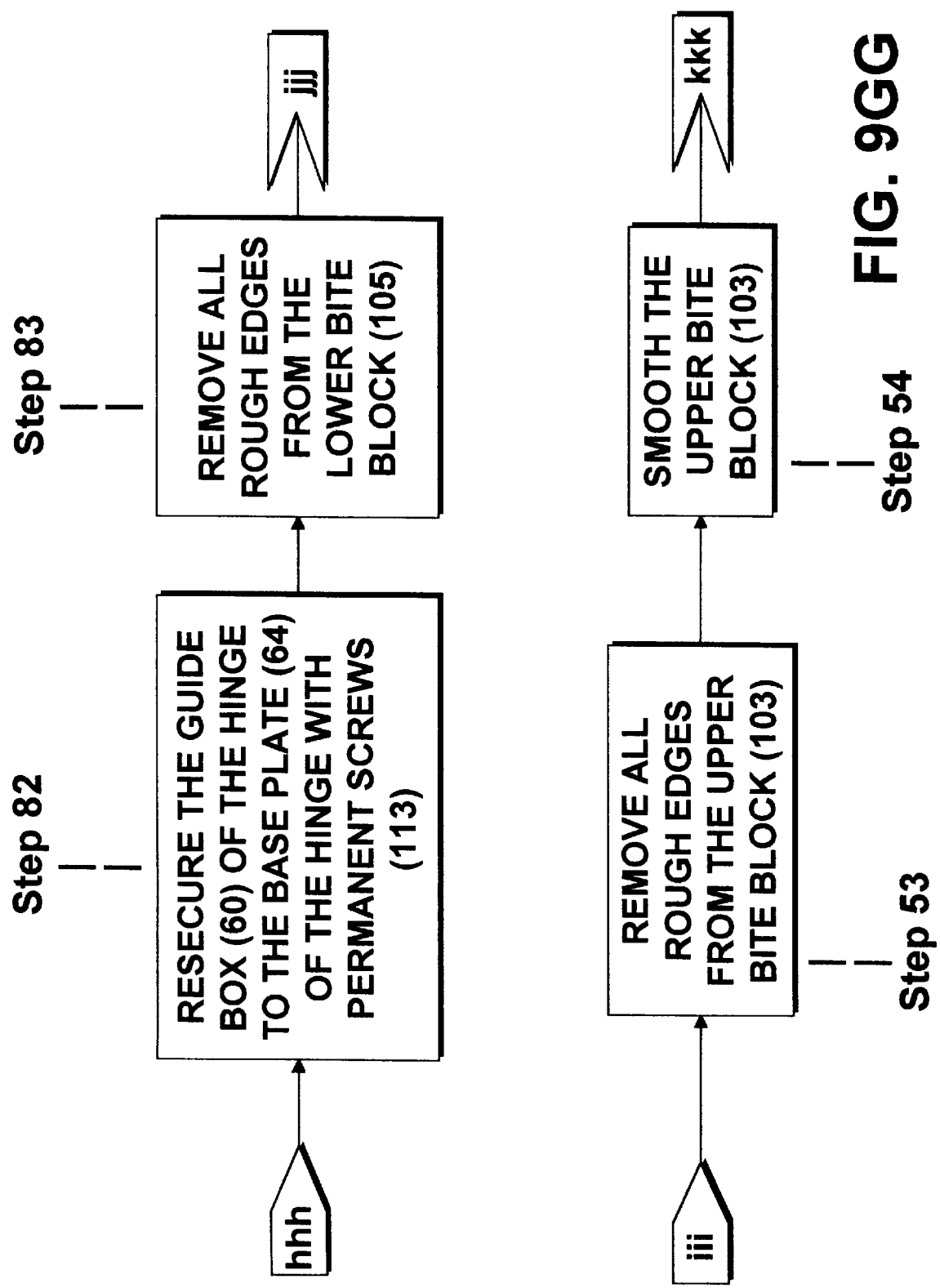
Figure 9I:
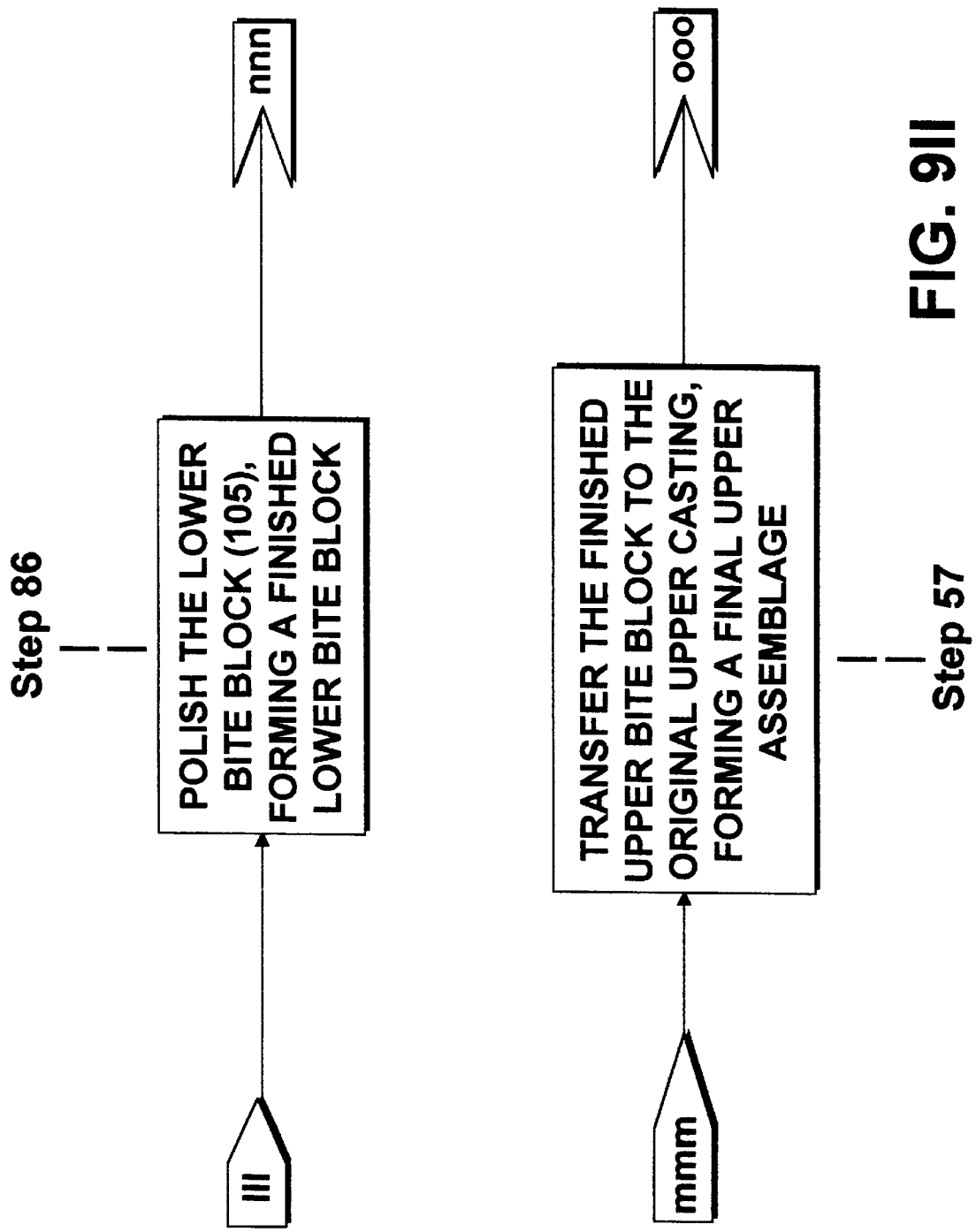
Figure 9L:
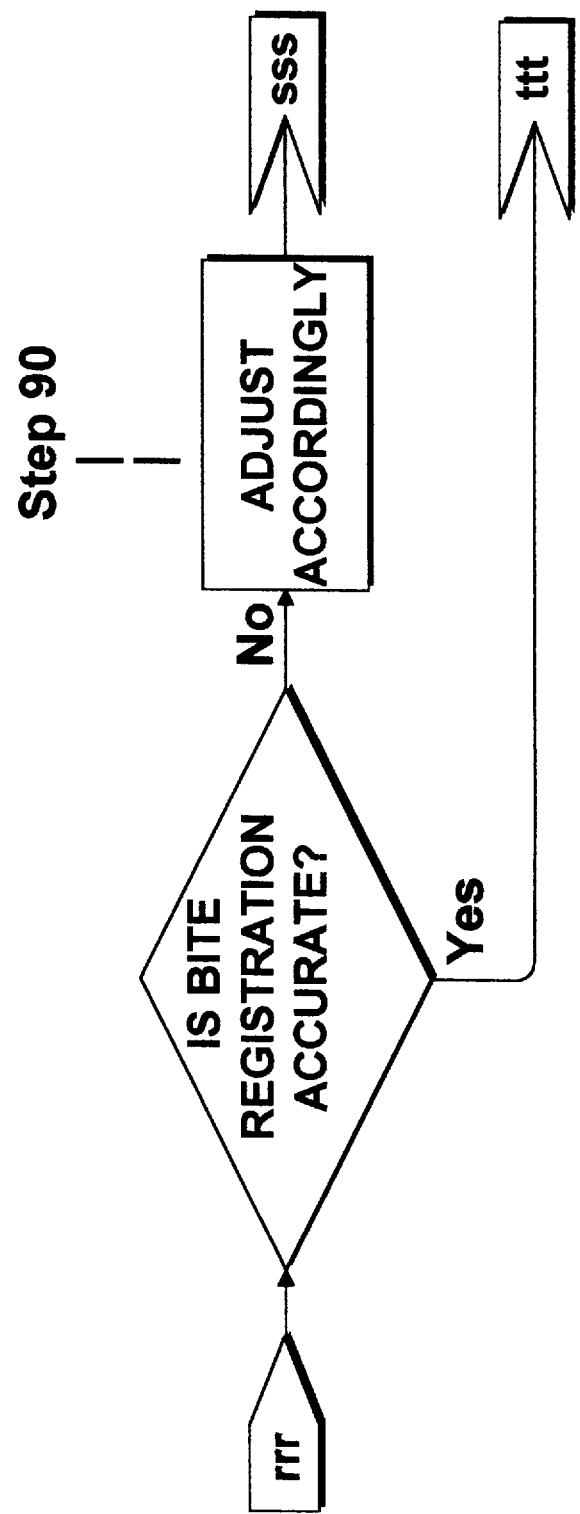
Figure 9M:
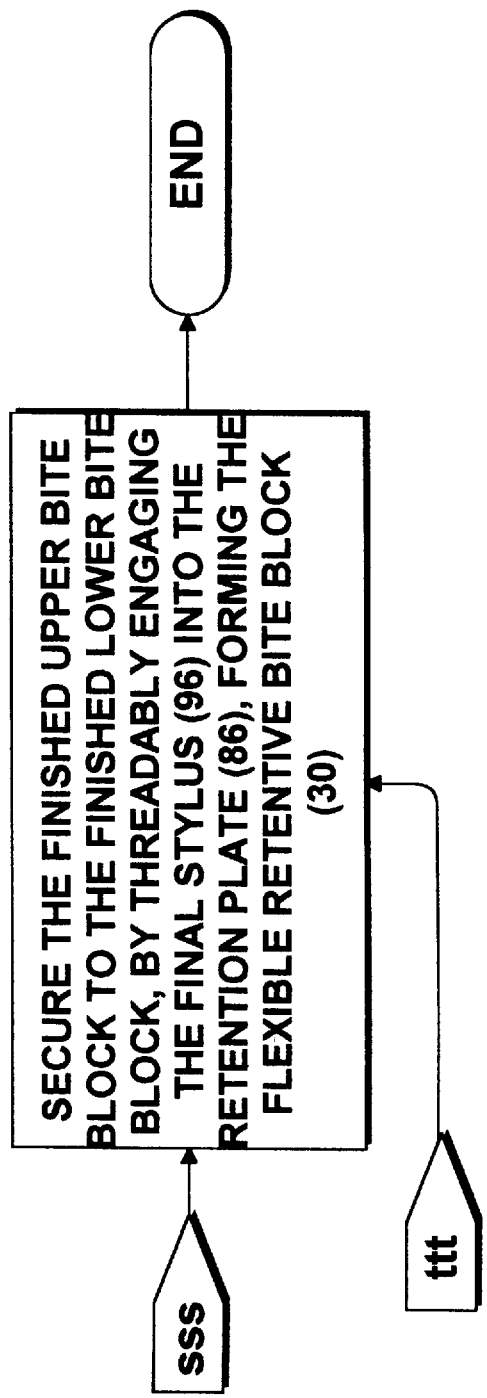

STEP 12: As shown in FIG. 6, position a lower processing stylus 58 in a guide box 60 of a hinge, wherein the lower processing stylus 58 has a narrow stub portion 62.

STEP 13: As shown in FIG. 6, secure the guide box 60 of the hinge to a base plate 64 of the hinge, by processing screws 66.

STEP 14: As shown in FIG. 6, secure the base plate 64 of the hinge to the lower duplicate casting 38, utilizing the wax luting agent, forming a lower assemblage 67.

STEP 15: Make a optional duplicate of an original upper casting forming an upper duplicate casting 68 having a gum 70, teeth 72 with supra bulges 74 and posterior portions with bite surfaces.

STEP 16: As shown in FIG. 3, mount the upper duplicate casting 68 on the articulator 44.

STEP 17: As shown in FIG. 3, survey the upper duplicate casting 68, forming a surveying line 76 thereon.

STEP 18: As shown in FIG. 3, extend the surveying line 76 approximately 1 mm past the supra bulges 74 of the teeth 72 of the upper duplicate casting 68, toward the gum 70 of the upper duplicate casting 68, forming an extended surveying line 78.

STEP 19: Remove the upper duplicate casting 68 from the articulator 44.

STEP 20: As similarly shown in FIG. 4, put the upper duplicate casting 68 in the heat pressure former 50.

STEP 21: As similarly shown in FIG. 4, position at least one plastic spacer sheet 80 on the teeth 72 of the upper duplicate casting 68.

STEP 22: As similarly shown in FIG. 4, activate the heat pressure former 50 causing the at least one plastic spacer sheet 80 to melt and conform to the teeth 72 of the upper duplicate casting 68, forming a conformed plastic spacer layer 82 thereon.

STEP 23: Remove the upper duplicate casting 68 with the conformed plastic spacer layer 82 thereon from the heat pressure former 50.

STEP 24: As similarly shown in FIG. 5, affix a pair of opposing metal bite pads 84 on the conformed plastic spacer layer 82, at the bite surfaces of the posterior portions of the teeth 72 of the upper duplicate casting 68, utilizing the wax luting agent, and forming therewith an upper pattern 85 (see FIG. 6).

STEP 25: Replace the upper duplicate casting 68 with the upper pattern 85 thereon on the articulator 44.

STEP 26: As shown in FIG. 6, set a retention plate 86 on the lower processing stylus 58, with the narrow stub portion 62 of the lower processing stylus 58 removably entering into an aperture 88 in the retention plate 86 assuring proper alignment of the retention plate 86 when securing the retention plate 86 to the upper pattern 85.

STEP 27: As shown in FIG. 6, secure the retention plate 86 of the hinge to the upper pattern 85, utilizing the wax luting agent.

STEP 28: As shown in FIG. 6, position a part 90 of an upper processing jig 92 into the retention plate 86 of the hinge.

STEP 29: As shown in FIG. 6, secure the upper processing jig 92 to the retention plate 86, by passing a non-threaded portion 94 of a final stylus 96 through the upper processing jig 92, with a threaded portion 98 of the final stylus 96 threadably engaging the aperture 88 in the retention plate 86, forming an upper assemblage 100.

STEP 30: Remove the upper assemblage 100 from the articulator 44.

STEP 31: Apply the separating medium to exposed portions of the upper assemblage 100.

Figure 7:
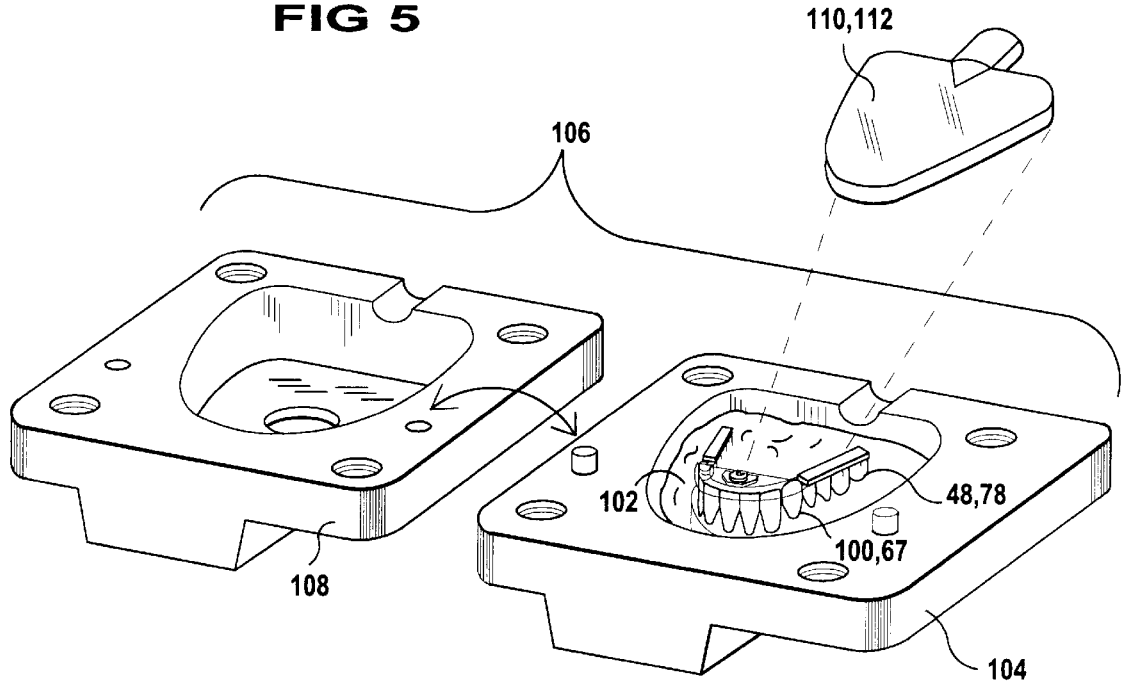
FIG. 7 is an exploded diagrammatic perspective view illustrating a flask being made ready for closure as further illustrated by steps of steps 62, 63, 64 and 65 of the fabrication process of the present invention.

STEP 32: As shown in FIG. 7, position stone 102 in a lower portion 104 of a flask 106 that has an upper portion 108.

STEP 33: As similarly shown in FIG. 7, place the upper assemblage 100 in the lower portion 104 of the flask 106.

STEP 34: As similarly shown in FIG. 7, place a wax sprue 110 on the upper assemblage 100.

STEP 35: As shown in FIG. 7, position additional stone 102 in the lower portion 104 of the flask 106 to the extended surveying line 78.

STEP 36: Apply the separating medium to exposed stone and the upper pattern 85.

STEP 37: Secure the upper portion 108 of the flask 106 to the lower portion 104 of the flask 106.

STEP 38: Fill the upper portion 108 of the flask 106 with additional stone 102.

STEP 39: Harden contents of the flask 106, forming an upper bite block mold.

STEP 40: Remove the wax luting agent and the wax sprue 110 from the upper bite block mold, utilizing boiling water, with the retention plate 86 of the hinge retained in the upper bite block mold.

STEP 41: Separate the upper portion 108 of the flask 106 from the lower portion 104 of the flask 106.

STEP 42: Pick out the conformed plastic spacer layer 80 and the pair of opposing metal bite pads 84 from the upper bite block mold.

STEP 43: Apply the separating medium to the upper bite block mold.

STEP 44: Preheat the upper portion 108 of the flask 106 and the lower portion 104 of the flask 106 under heat lamps.

STEP 45: Heat polyamide material forming preheated polyamide material. A typical polyamide material is sold by RAPID INJECTION SYSTEMS CORP.

STEP 46: Secure the upper portion 108 of the flask 106 to the lower portion 104 of the flask 106.

STEP 47: Inject the preheated polyamide material into the flask 106, forming an upper bite block 103 (see FIG. 8) having the retention plate 86 of the hinge embedded therein.

STEP 48: Cool the flask 106.

STEP 49: Separate the upper portion 108 of the flask 106 from the lower portion 104 of the flask 106.

STEP 50: Remove the upper bite block 103 from the upper bite block mold.

STEP 51: Remove the final stylus 96.

STEP 52: Remove the processing jig 92.

STEP 53: Remove all rough edges from the upper bite block 103.

STEP 54: Smooth the upper bite block 103.

STEP 55: Check and adjust the upper bite block 103, as required.

STEP 56: Polish the upper bite block 103, forming a finished upper bite block.

STEP 57: Transfer the finished upper bite block to the original upper casting, forming a final upper assemblage.

STEP 58: Put the final upper assemblage On the articulator 44.

STEP 59: Remove the lower assemblage 67 from the articulator 44.

STEP 60: Apply the separating medium to exposed portions of the lower assemblage 67.

STEP 61: As shown in FIG. 7, position stone 102 in the lower portion 104 of the flask 106.

STEP 62: As shown in FIG. 7, place the lower assemblage 67 in the lower portion 104 of the flask 106.

STEP 63: As shown in FIG. 7, place a wax sprue 112 on the lower assemblage 67.

STEP 64: Position additional stone 102 in the lower portion 104 of the flask 106 to the extended surveying line 48.

STEP 65: Apply the separating medium to exposed stone and the lower pattern 66.

STEP 66: Secure the upper portion 108 of the flask 106 to the lower portion 104 of the flask 106.

STEP 67: Fill the upper portion 108 of the flask 106 with additional stone 102.

STEP 68: Harden contents of the flask 106, forming a lower bite block mold.

STEP 69: Remove the wax luting agent and the wax sprue 112 from the lower bite block mold, utilizing boiling water, with the base plate 64 of the hinge retained in the lower bite block mold.

STEP 70: Separate the upper portion 108 of the flask 106 from the lower portion 104 of the flask 106.

STEP 71: Pick out the conformed plastic spacer layer 54 and the pair of opposing metal bite pads 56 from the lower bite block mold.

STEP 72: Apply the separating medium to the lower bite block mold.

STEP 73: Preheat the upper portion 108 of the flask 106 and the lower portion 104 of the flask 106 under the heat lamps.

STEP 74: Heat polyamide material forming preheated polyamide material.

STEP 75: Secure the upper portion 108 of the flask 106 to the lower portion 104 of the flask 106.

STEP 76: Inject the preheated polyamide material into the flask 106 forming a lower bite block 105 (see FIG. 8) having the base plate 64 of the hinge embedded therein.

STEP 77: Cool the flask 106.

STEP 78: Separate the upper portion 108 of the flask 106 from the lower portion 104 of the flask 106.

STEP 79: Remove the lower bite block 105 from the lower bite block mold.

STEP 80: Remove the processing screws 66, freeing the guide box 60 and the lower processing stylus 58.

STEP 81: As shown in FIG. 8, replace the lower processing stylus 58 with the final stylus 96.

STEP 82: As shown in FIG. 8, resecure the guide box 60 of the hinge to the base plate 64 of the hinge with permanent screws 106.

STEP 83: Remove all rough edges from the lower bite block 105.

STEP 84: Smooth the lower bite block 105.

STEP 85: Check and adjust the lower bite block 105, as required.

STEP 86: Polish the lower bite block 105, forming a finished lower bite block.

STEP 87: Transfer the finished lower bite block to the original lower casting, forming a final lower assemblage.

STEP 88: Put the final lower assemblage in the articulator 44.

STEP 89: Verify accuracy of bite registration of finished upper bite block and finished lower bite block, i.e. is bite registration accurate?.

STEP 90 Adjust accordingly, if answer to step 89 is no.

STEP 91 Secure the finished upper bite block to the finished lower bite block by threadably engaging the final stylus 96 into the retention plate 86, if answer to step 89 is yes, forming the flexible retentive bite block 30.

The configurations of the base plate 64, the guide box 60, and the retention plate 86 is of that taught by U.S. Pat. No. 5,365,945 to Halstrom. The configurations of the processing stylus 58, the processing screws 66, the processing jig 92, the final stylus 96, and the permanent screws 106, however, are different and will be discussed with reference to FIGS. 6 and 8.

As shown in FIG. 6, the processing stylus 58 has a head 114 that fills a milled-out cavity 116 in the guide box 60, and a shaft 118 that is non-threaded and extends coaxially from and is narrower than the head 1114 and enters a kidney-shaped aperture 120 in an upper surface 122 of the guide box 60, wherein the narrow stub portion 62 is non-threaded and extends coaxially from and is narrower than the shaft 118.

As shown in FIG. 6, each of the processing screws 66 has a head 124, a shaft 126 that is non-threaded and extends coaxially from and is narrower than the head 124 and passes through a respective outermost non-threaded aperture 128 of a pair of outermost non-threaded apertures 128 of three non-threaded apertures 128 in the base plate 64, a stub portion 130 that is threaded and extends coaxially from and is narrower than the shaft 126 and threadably engages a respective threaded aperture 132 of a pair of threaded apertures 132 in the guide box 60, and a shaft 134 that is non-threaded and extends coaxially from and is narrower than the stub portion 130 and extends past the upper surface 122 of the guide box 60 so as to prevent casting material from entering the pair of threaded apertures 132 in the guide box 60 during processing.

As shown in FIG. 6, the processing jig 92 has a base 136 that is flat, thin, and has a center portion 138 that is circular-shaped with an aperture 140 and a pair of opposing wing portions 142 that are rectangular-shaped and extend coplanarly from the center portion 138 of the base 136, wherein the part 90 of the processing jig 92 is a plurality of stub portions 144 that are cylindrically-shaped, spaced-apart, and extend perpendicularly from the base 136 and fill the aperture 88 in the retention plate 86 so as to prevent casting material from entering the aperture 88 in the retention plate 86 during processing.

As shown in FIG. 8, the final stylus 96 has a head 146 that is circular-shaped and moves laterally in the milled-out cavity 116 in the guide box 60, wherein the non-threaded portion 94 is a shaft 94 that extends coaxially from and is narrower than the head 146 and moves laterally in the kidney-shaped aperture 120 in the upper surface 122 of the guide box 60, and wherein the threaded portion 98 is a stub portion 98 that extends coaxially from and is narrower than the shaft 94 and threadably engages the aperture 88 in the retention plate 86.

As shown in FIG. 8, each of the permanent screws 113 has a head 148 that is circular-shaped and recessed in a respective outermost aperture of three non-threaded apertures in the lower bite block 105, a shaft 150 that is non-threaded and extends coaxially from and is narrower than the head 148 and passes through the respective outermost non-threaded aperture 128 of the pair of outermost non-threaded apertures 128 of the three non-threaded apertures 128 in the base plate 164, and a stub portion 152 that is threaded and extends coaxially from and is narrower than the shaft 150 and threadably engages the respective threaded aperture 132 of the pair of threaded apertures 132 in the guide box 60.

It will be understood that each of the elements described above, or two or more together, may also find a useful application in other types of constructions differing from the types described above.

While the invention has been illustrated and described as embodied in a flexible retentive bite block and fabrication process, however, it is not limited to the details shown, since it will be understood that various omissions, modifications, change in the order of steps, change in the number of or necessarity of optional duplicate castings, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A method of fabricating a flexible retentive bite block, comprising the steps of:
   a) making an optional duplicate of an original lower casting, forming a lower duplicate casting having a gum and teeth with supra bulges and posterior portions with bite surfaces;
   b) mounting said lower duplicate casting on an articulator;
   c) surveying said lower duplicate casting, forming a surveying line thereon;
   d) extending said surveying line approximately 1 mm past said supra bulges of said teeth of said lower duplicate casting, toward said gum of said lower duplicate casting, forming an extended surveying line;
   e) removing said lower duplicate casting from the articulator;
   f) putting said lower duplicate casting in a heat pressure former;
   g) positioning at least one plastic spacer sheet on said teeth of said lower duplicate casting;
   h) activating the heat pressure former causing said at least one plastic spacer sheet to melt and conform to said teeth of said lower duplicate casting, forming a conformed plastic spacer layer thereon;
   i) removing said lower duplicate casting with said conformed plastic spacer layer thereon from the heat pressure former;
   j) affixing a pair of opposing metal bite pads on said conformed plastic spacer layer, at said bite surfaces of said posterior portions of said teeth of said lower duplicate casting, utilizing a wax luting agent, and forming with said conformed plastic spacer layer and said wax luting agent a lower pattern;
   k) replacing said lower duplicate casting with said lower pattern thereon on the articulator;
   l) positioning a lower processing stylus in a guide box of a hinge wherein said lower processing stylus has a narrow stub portion;
   m) securing said guide box of said hinge to a base plate of said hinge, by processing screws; and
   n) securing said base plate of said hinge to said lower duplicate casting, utilizing said wax luting agent, forming a lower assemblage.

2. The method as defined in claim 1; further comprising the steps of:
   a) making an optional duplicate of an original upper casting, forming an upper duplicate casting having a gum and teeth with supra bulges and posterior portions with bite surfaces;
   b) mounting said upper duplicate casting on the articulator;
   c) surveying said upper duplicate casting, forming a surveying line thereon;
   d) extending said surveying line approximately 1 mm past said supra bulges of said teeth of said upper duplicate casting, toward said gum of said upper duplicate casting, forming an extended surveying line;
   e) removing said upper duplicate casting from the articulator;
   f) putting said upper duplicate casting in the heat pressure former;
   g) positioning at least one plastic spacer sheet on said teeth of said upper duplicate casting;
   h) activating the heat pressure former causing said at least one plastic spacer sheet to melt and conform to said teeth of said upper duplicate casting, forming a conformed plastic spacer layer thereon;
   i) removing said upper duplicate casting with said conformed plastic spacer layer thereon from the heat pressure former;
   j) affixing a pair of opposing metal bite pads on said conformed plastic spacer layer, at said bite surfaces of said posterior portions of said teeth of said upper duplicate casting, utilizing said wax luting agent, and forming with the conformed plastic spacer layer and the wax luting agent an upper pattern; and
   k) replacing said upper duplicate casting with said upper pattern thereon on the articulator.

3. The method as defined in claim 2; further comprising the steps of:
   a) setting a retention plate of said hinge on said lower processing stylus, with said narrow stub portion of said lower processing stylus removably entering into an aperture in said retention plate of said hinge, assuring proper alignment of said retention plate of said hinge when securing said retention plate of said hinge to said upper pattern;
   b) securing said retention plate of said hinge to said upper pattern, utilizing the wax luting agent;
   c) positioning a part of an upper processing jig into said retention plate of said hinge; and
   d) securing said upper processing jig to said retention plate of said hinge, by passing a non-threaded portion of a final stylus of said hinge through said upper processing jig, with a threaded portion of said final stylus of said hinge threadably engaging said aperture in said retention plate of said hinge, forming an upper assemblage.

4. The method as defined in claim 3; further comprising the steps of:
   a) removing said upper assemblage from the articulator;
   b) applying the separating medium to exposed portions of said upper assemblage;
   c) positioning stone in a lower portion of a flask having an upper portion;
   d) placing said upper assemblage in the lower portion of the flask;
   e) placing a wax sprue on said upper assemblage;
   f) positioning additional stone in the lower portion of the flask to said extended surveying line on said upper assemblage;
   g) applying the separating medium to exposed stone and said upper pattern;
   h) securing the upper portion of the flask to the lower portion of the flask;
   i) filling the upper portion of the flask with additional stone;
   j) hardening contents of the flask, forming an upper bite block mold;
   k) removing the wax luting agent and the wax sprue from said upper bite block mold utilizing boiling water, with said retention plate of said hinge retained in said upper bite block mold;
   l) separating the upper portion of the flask from the lower portion of the flask;
   m) picking out said conformed plastic spacer layer and said pair of opposing metal bite pads from said upper bite block mold;
   n) applying the separating medium to said upper bite block mold;
   o) preheating the upper portion of the flask and the lower portion of the flask, under heat lamps;
   p) heat a polyamide material, forming preheated polyamide material;
   q) securing the upper portion of the flask to the portion of the flask;
   r) injecting said preheated polyamide material into the flask, forming an upper bite block having said retention plate of said hinge embedded therein;
   s) cooling the flask;
   t) separating the upper portion of the flask from the lower portion of the flask;
   u) removing said upper bite block from said upper bite block mold;
   v) removing said final stylus of said hinge; and
   w) removing said processing jig.

5. The method as defined in claim 4; further comprising the steps of:
   a) removing all rough edges from said upper bite block;
   b) smoothing said upper bite block;
   c) checking and adjusting said upper bite block, as required;
   d) polishing said upper bite block, forming a finished upper bite block;
   e) transferring said finished upper bite block to the original upper casting, forming a final upper assemblage; and
   f) putting said final upper assemblage on the articulator.

6. The method as defined in claim 5; further comprising the steps of:
   a) removing said lower assemblage from the articulator;
   b) applying the separating medium to exposed portions of said lower assemblage;
   c) positioning stone in the lower portion of the flask;
   d) placing said lower assemblage in the lower portion of the flask;
   e) placing a wax sprue on said lower assemblage;
   f) positioning additional stone in the lower portion of the flask to said extended surveying line on said lower assemblage;
   g) applying the separating medium to exposed stone and said lower pattern;
   h) securing the upper portion of the flask to the lower portion of the flask;
   i) filling the upper portion of the flask with additional stone;
   j) hardening contents of the flask, forming a lower bite block mold;
   k) removing said wax luting agent and said wax sprue from said lower bite block mold, utilizing boiling water, with said base plate of said hinge retained in said lower bite block mold;
   l) separating the upper portion of the flask from the lower portion of the flask;
   m) picking out said conformed plastic spacer layer and said pair of opposing metal bite pads bite pads from said lower bite block mold;
   n) applying the separating medium to said lower bite block mold;
   o) preheating the upper portion of the flask and the lower portion of the flask, under the heat lamps;
   p) heat said polyamide material, forming said preheated polyamide material;
   q) securing the upper portion of the flask to the lower portion of the flask;
   r) injecting said preheated polyamide material into the flask, forming a lower bite block having said lower plate of said hinge embedded therein;
   s) cooling the flask;
   t) separating the upper portion of the flask from the lower portion of the flask;
   u) remove said lower bite block from said lower bite block mold;
   v) removing said processing screws, freeing said guide box of said hinge and said lower processing stylus;

w) replacing said lower processing stylus with said final stylus of said hinge; and x) resecuring said guide box of said hinge to said base plate of said hinge, utilizing permanent screws.

7. The method as defined in claim 6; further comprising the steps of:

a) removing all rough edges from said lower bite block;

b) smoothing said lower bite block;

c) checking and adjusting said lower bite block, as required;

d) polishing said lower bite block, forming a finished lower bite block;

e) transferring said finished lower bite block to the original lower casting, forming a final lower assemblage; and f) putting said final lower assemblage on the articulator.

8. The method as defined in claim 7; further comprising the steps of:

a) verifying accuracy of bite registration of said finished upper bite block and said finished lower bite block;

b) determining bite registration accuracy;

c) adjusting accordingly, if answer to step b) is no; and d) securing said finished upper bite block to said finished lower bite block, by threadably engaging said final stylus of said hinge into said retention plate of said hinge, if answer to step b) is yes, forming said flexible retentive bite block.

9. The method as defined in claim 6, wherein each permanent screw of said permanent screws comprises:

a) a head that is circular-shaped and recessed in a respective outermost aperture of three non-threaded apertures in said lower bite block;

b) a shaft that is non-threaded and extends coaxially from and is narrower than said head of said permanent screw, and passes through a respective outermost non-threaded aperture of a pair of outermost non-threaded apertures of three non-threaded apertures in the base plate; and c) a stub portion that is threaded and extends coaxially from and is narrower than said shaft and threadably engages a respective threaded aperture of a pair of threaded apertures in the guide box.

10. The method as defined in claim 3, wherein said processing stylus comprises:

a) a head that fills a milled-out cavity in said guide box; and b) a shaft that is non-threaded and extends coaxially from and is narrower than said head of said processing stylus, and enters a kidney-shaped aperture in an upper surface of said guide box;

wherein said narrow stub portion of said processing stylus is non-threaded and extends coaxially from and is narrower than said shaft of said processing stylus, and non-threadably enters said aperture in said retention plate, assuring proper alignment of said retention plate when securing said retention plate to said upper pattern.

11. The method as defined in claim 3, wherein said processing jig comprises a base that is flat, thin, and has a center portion with an aperture and a pair of opposing wing portions that are rectangular-shaped and extend coplanarly from said center portion of said base of said processing jig; wherein said part of said processing jig is a plurality of stub portions that are cylindrically-shaped, spaced-apart, and extend perpendicularly from said base of said processing jig, and fill a plurality of apertures in the retention plate.

12. The method as defined in claim 3, wherein said final stylus comprises a head that is circular-shaped and moves laterally in a milled-out cavity in said guide box;

wherein said non-threaded portion of said final stylus is a shaft that extends coaxially from and is narrower than said head of said final stylus, and moves laterally in a kidney-shaped aperture in an upper surface of the guide box; and wherein said threaded portion of said f portion that extends coaxially from and is narrower than said shaft of said final stylus, and threadably engages a threaded aperture of a plurality of threaded apertures in said retention plate.

13. The method as defined in claim 1, wherein each processing screw of said pair of processing screws comprises:

a) a head;

b) a shaft that is non-threaded and extends coaxially from and is narrower than said head of said processing screw, and passes through a respective outermost non-threaded aperture of a pair of outermost non-threaded apertures of three non-threaded apertures in said base plate;

c) a stub portion that is threaded and extends coaxially from and is narrower than said shaft of said processing screw, and threadably engages a respective threaded aperture of a pair of threaded apertures in said guide box; and d) a shaft that is non-threaded and extends coaxially from and is narrower than said stub portion of said processing screw, and extends past an upper surface of said guide box so as to prevent casting material from entering a pair of threaded apertures in said guide box during processing.

14. A method of fabricating a flexible retentive bite block having an upper bite block shaped to conform to the maxillary detention, a lower bite block shaped to conform to the mandibular detention and having three non-threaded apertures, and a hinge adjustably connecting the upper bite block to the lower bite block, the hinge comprising a retention plate affixed to the upper bite block and having a plurality of threaded apertures, a base plate affixed to the lower bite block and having three non-threaded apertures in alignment with the three non-threaded apertures in the lower bite block, and a guide box affixed to the upper bite block and the lower bite block and having a kidney-shaped aperture formed on its upper surface and a milled-out cavity formed beneath the aperture in the upper surface of the guide block and a pair of threaded apertures straddling the milled-out cavity in the guide box and being in alignment with the outermost non-threaded apertures of the three non-threaded apertures in the base plate, comprising the step of molding the upper bite block and the lower bite block from polyamide whose inherent flexibility eliminates the need for dental wires and the problems associated therewith.

15. The method as defined in claim 14; further comprising the step of assuring proper positioning of the retention plate by utilizing a processing stylus which comprises:

a) a head that fills the milled-out cavity in the guide box;

b) a shaft that is non-threaded and extends coaxially from and is narrower than said head of said processing stylus, and enters the kidney-shaped aperture in the upper surface of the guide box; and c) a narrow stub portion that is non-threaded and extends coaxially from and is narrower than said shaft of said processing stylus, and non-threadably enters an aperture of the plurality of apertures in the retention plate.

16. The method as defined in claim 14; further comprising the step of connecting the guide box to the base plate by utilizing a pair of processing screws, wherein each processing screw of the pair of processing screws comprises:

a) a head;

b) a shaft that is non-threaded and extends coaxially from and is narrower than said head of said processing screw, and passes through a respective outermost non-threaded aperture of a pair of outermost non-threaded apertures of the three non-threaded apertures in the base plate;

c) a stub portion that is threaded and extends coaxially from and is narrower than said shaft of said processing screw, and threadably engages a respective threaded aperture of the pair of threaded apertures in the guide box; and d) a shaft that is non-threaded and extends coaxially from and is narrower than said stub portion of said processing screw, and extends past the upper surface of the guide box.

17. The method as defined in claim 14; further comprising the step of preventing casting material from entering the plurality of threaded apertures in the retention plate by utilizing a processing jig which comprises:

a) a base that is flat, thin, and has a center portion with an aperture and a pair of opposing wing portions that are rectangular-shaped and extend coplanarly from said center portion of said base of said processing jig; and b) a plurality of stub portions that are cylindrically-shaped, spaced-apart, and extend perpendicularly from said base of said processing jig, and fill the plurality of apertures in the retention plate.

18. The method as defined in claim 14; further comprising the step of adjustably connecting the guide box to the retention plate by utilizing a final stylus which comprises:

a) a head that is circular-shaped and moves laterally in the milled-out cavity in the guide box;

b) a shaft that is non-threaded and extends coaxially from and is narrower than said head of said final stylus, and moves laterally in the kidney-shaped aperture in the upper surface of the guide box; and c) a stub portion that is threaded and extends coaxially from and is narrower than said shaft of said final stylus, and threadably engages a threaded aperture of the plurality of threaded apertures in the retention plate.

19. The method as defined in claim 14; further comprising the step of connecting the guide box to the base plate by utilizing a pair of permanent screws, wherein each permanent screw of the pair of permanent screws comprises:

a) a head that is circular-shaped and recessed in a respective outermost aperture of the three non-threaded apertures in the lower bite block;

b) a shaft that is non-threaded and extends coaxially from and is narrower than said head of said permanent screw, and passes through a respective outermost non-threaded aperture of a pair of outermost non-threaded apertures of the three non-threaded apertures in the base plate; and c) a stub portion that is threaded and extends coaxially from and is narrower than said shaft of said permanent screw, and threadably engages a respective threaded aperture of the pair of threaded apertures in the guide box.

20. An improved flexible retentive bite block of the type having an upper bite block shaped to conform to the maxillary detention, a lower bite block shaped to conform to the mandibular detention and having three non-threaded apertures, and a hinge adjustably connecting the upper bite block to the lower bite block, the hinge comprising a retention plate affixed to the upper bite plate and having a plurality of threaded apertures, a base plate affixed to the lower bite plate and having three non-threaded apertures in alignment with the three non-threaded apertures in the lower bite plate, and a guide box affixed to the upper bite block and the lower bite block and having a kidney-shaped aperture formed on its upper surface and a milled-out cavity formed beneath the aperture in the upper surface of the guide block and a pair of threaded apertures straddling the milled-out cavity in the guide box and being in alignment with the outermost non-threaded apertures of the three non-threaded apertures in the base plate, wherein the improvement comprising the upper bite block and lower bite block being made of polyamide whose inherent flexibility eliminates the need for dental wires and the problems associated therewith.

21. The improved retentive bite block as defined in claim 20, wherein the improvement further comprises a processing stylus for assuring proper positioning of the retention plate during fabrication which comprises:

a) a head that fills the milled-out cavity in the guide box;

b) a shaft that is non-threaded and extends coaxially from and is narrower than said head of said processing stylus, and enters the kidney-shaped aperture in the upper surface of the guide box; and c) a narrow stub portion that is non-threaded and extends coaxially from and is narrower than said shaft of said processing stylus, and non-threadably enters an aperture of the plurality of apertures in the retention plate.

22. The improved retentive bite block as defined in claim 20, wherein the improvement further comprises a pair of processing screws for connecting the guide box to the base plate, wherein each processing screw of the pair of permanent screws comprises:

a) a head;

b) a shaft that is non-threaded and extends coaxially from and is narrower than said head of said processing screw, and passes through a respective outermost non-threaded aperture of a pair of outermost non-threaded apertures of the three non-threaded apertures in the base plate;

c) a stub portion that is threaded and extends coaxially from and is narrower than said shaft of said processing screw, and threadably engages a respective threaded aperture of the pair of threaded apertures in the guide box; and d) a shaft that is non-threaded and extends coaxially from and is narrower than said stub portion of said processing screw, and extends past the upper surface of the guide box.

23. The improved retentive bite block as defined in claim 20, wherein the improvement further comprises a processing jig for preventing casting material from entering the plurality of threaded apertures in the retention plate which comprises:

a) a base that is flat, thin, and has a center portion with an aperture and a pair of opposing wing portions that are rectangular-shaped and extend coplanarly from said center portion of said base of said processing jig; and b) a plurality of stub portions that are cylindrically-shaped, spaced-apart, and extend perpendicularly from said base of said processing jig, and fill the plurality of apertures in the retention plate.

24. The improved retentive bite block as defined in claim 20, wherein the improvement further comprises a final stylus for adjustably connecting the guide box to the retention plate comprising:

a) a head that is circular-shaped and moves laterally in the milled-out cavity in the guide box;
b) a shaft that is non-threaded and extends coaxially from and is narrower than said head of said final stylus, and moves laterally in the kidney-shaped aperture in the upper surface of the guide box; and
c) a stub portion that is threaded and extends coaxially from and is narrower than said shaft of said final stylus, and threadably engages a threaded aperture of the plurality of threaded apertures in the retention plate.

25. The improved retentive bite block as defined in claim 20, wherein the improvement further comprises a pair of permanent screws for connecting the guide box to the base plate, wherein each permanent screw of the pair of permanent screws comprises:

a) a head that is circular-shaped and recessed in a respective outermost aperture of the three non-threaded apertures in the lower bite block;
b) a shaft that is non-threaded and extends coaxially from and is narrower than said head of said permanent screw, and passes through a respective outermost non-threaded aperture of a pair of outermost non-threaded apertures of the three non-threaded apertures in the base plate; and
c) a stub portion that is threaded and extends coaxially from and is narrower than said shaft of said permanent screw, and threadably engages a respective threaded aperture of the pair of threaded apertures in the guide box.

* * * * *